United States Patent
Wagner

(10) Patent No.: US 8,529,877 B2
(45) Date of Patent: Sep. 10, 2013

(54) BENZYLIDENE COMPOUNDS COMPRISING PHOSPHONO-GROUPS

(75) Inventor: Barbara Wagner, Lörrach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/127,988

(22) PCT Filed: Nov. 4, 2009

(86) PCT No.: PCT/EP2009/064593
§ 371 (c)(1),
(2), (4) Date: May 23, 2011

(87) PCT Pub. No.: WO2010/054966
PCT Pub. Date: May 20, 2010

(65) Prior Publication Data
US 2011/0212039 A1    Sep. 1, 2011

(30) Foreign Application Priority Data
Nov. 13, 2008  (EP) .................................... 08168990

(51) Int. Cl.
*A61K 8/00*  (2006.01)

(52) U.S. Cl.
USPC ....................................................... 424/70.1

(58) Field of Classification Search
None
See application file for complete search history.

(56) References Cited

U.S. PATENT DOCUMENTS
2005/0260144 A1    11/2005   Huber

FOREIGN PATENT DOCUMENTS
FR    2 142 987 A    2/1973
GB    1 375 270 A    11/1974
WO    94/19358 A    9/1994
WO    2004/026245 A    4/2004

OTHER PUBLICATIONS
Danion et al., Tetrahedron Letters vol. 43, 1968, pp. 4537-4540.
Lehnert et al., Tetrahedron Letters vol. 30, 1974, pp. 301-305.

*Primary Examiner* — Paul Dickinson
(74) *Attorney, Agent, or Firm* — Shiela A. Loggins

(57) ABSTRACT

Disclosed is the use of benzylidene compounds comprising phosphono-groups for the protecting of human and animal hair and skin from UV radiation. The UV filters of the present invention represent oil-soluble substances which advantageously absorb in the UV-A and UV-B region.

6 Claims, 1 Drawing Sheet (1)

(1a)

Set-up for irradiation of the samples. 1: metal halide lamp (Macam Flexicure), 2: liquid light guide, 3: optical bench, 4: cut-off filter, translucent for λ > 290 nm, 5: closed cuvette with UV-absorber solution, 6: magnetic stirrer Set-up for irradiation of the samples. 1: metal halide lamp (Macam Flexicure), 2: liquid light guide, 3: optical bench, 4: cut-off filter, translucent for λ > 290 nm, 5: closed cuvette with UV-absorber solution, 6: magnetic stirrer
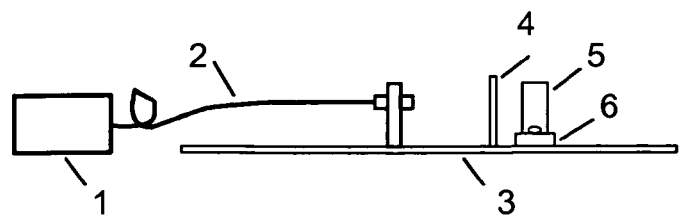

BENZYLIDENE COMPOUNDS COMPRISING PHOSPHONO-GROUPS

The present invention relates to the use of benzylidene compounds comprising phosphono-groups for cosmetic preparations.

It is well known that ultraviolet radiation (light) is harmful to human skin. Depending on the wavelength the UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter and a broad band UV filter covering the full range of about 290 nm to about 400 nm to prevent the human skin from damaging by the sunlight.

Unfortunately, many effective organic UV filters have a poor oil-solubility at a certain concentration and tend to crystallization. As a consequence the UV protection efficacy is significantly decreased.

Moreover the oil soluble UV filters should be included in cosmetic sun care products without any impact on the sensorial characteristic of the emulsion. For that reason the optimal distribution of the UV absorber within the hydro-lipid film left on the skin after spreading should be guaranteed.

It is therefore an object of the present invention to find UV absorber formulations which have improved properties regarding the UV absorber.

Surprisingly it has been found that specific benzylidene compounds which comprise phosphono groups have very good properties as cosmetic UV absorbers.

Therefore, the present invention relates to the use of benzylidene compounds of formula

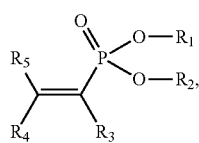

(1)

wherein $R_1$ and $R_2$ independently of one another are hydrogen; unsubstituted or substituted $C_1$-$C_{12}$alkyl; unsubstituted or substituted $C_3$-$C_{12}$cycloalkyl; unsubstituted or substituted $C_6$-$C_{20}$aryl; or unsubstituted or substituted $C_2$-$C_{20}$alkenyl;

$R_3$ is $PO_3R_1R_2$; $COOR_6$; $COR_7$; $CONR_7R_8$; —$SO_2R_6$; CN; unsubstituted or substituted $C_6$-$C_{20}$aryl;

$R_4$ is unsubstituted $C_6$-$C_{20}$aryl; or $C_6$-$C_{20}$aryl which is substituted by at least one $C_1$-$C_{18}$alkyl, $C_1$-$C_{18}$alkoxy, $C_3$-$C_{12}$cycloalkyl, hydroxy, amino, mono- or di-$C_1$-$C_{18}$alkylamino, —$NR_{10}COR_{11}$ or the radical of formula

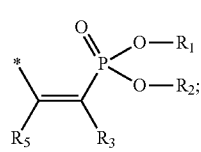

(1a)

or unsubstituted or substituted $C_4$-$C_{20}$heteroaryl;

$R_5$ is hydrogen; substituted or unsubstituted $C_1$-$C_{20}$alkyl; unsubstituted or substituted $C_3$-$C_{12}$cycloalkyl; unsubstituted or substituted $C_6$-$C_{20}$aryl; or unsubstituted or substituted $C_4$-$C_{20}$heteroaryl; or $R_4$ and $R_5$ form a cycloaliphatic ring;

$R_6$, $R_7$ and $R_8$ independently from each other are hydrogen; $C_1$-$C_{18}$alkyl or $C_3$-$C_{12}$cycloalkyl, which may be substituted by one or more E and/or interrupted by one or more D; or $C_6$-$C_{20}$aryl, which may be substituted by G; or $R_7$ and $R_8$ together form a five or six membered ring;

D is —CO—; —COO—; —S—; —SO—; —SO$_2$—; —O—; —NR$_9$—; —$SiR_{12}R_{13}$—; —POR$_{14}$—; —CR$_{15}$=CR$_{16}$—; or —C≡C—;

E is —OR$_{17}$; —SR$_{17}$; —NR$_{10}$R$_{11}$; —NR$_{10}$COR$_{11}$; —COR$_{11}$; —COOR$_{11}$; —CONR$_{10}$R$_{11}$; —CN; halogen; SO$_3$R$_{18}$; SO$_2$R$_{18}$; PO$_3$(R$_{18}$)$_2$; or PO$_2$(R$_{18}$)$_2$;

G is E; $C_1$-$C_{18}$alkyl, which is optionally interrupted by D; $C_1$-$C_{18}$perfluoroalkyl; $C_1$-$C_{18}$alkoxy, which is optionally substituted by E and/or interrupted by D; wherein $R_9$, $R_{10}$ and $R_{11}$, independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or $R_{10}$ and $R_{11}$ together form a five or six membered ring;

$R_{12}$ and $R_{13}$ independently of each other are hydrogen; $C_1$-$C_{18}$alkyl; or $C_6$-$C_{18}$aryl which is optionally substituted by $C_1$-$C_{18}$alkyl;

$R_{14}$ is $C_1$-$C_{18}$alkyl; or $C_6$-$C_{18}$aryl, which is optionally substituted by $C_1$-$C_{18}$alkyl;

$R_{15}$ and $R_{16}$ independently of each other are hydrogen; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;

$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—; and $R_{18}$ is hydrogen; $C_6$-$C_{18}$aryl, which is optionally substituted by $C_1$-$C_{18}$alkyl or $C_1$-$C_{18}$alkoxy; or $C_1$-$C_{18}$alkyl, which is optionally interrupted by —O—;

for the protecting of human and animal hair and skin from UV radiation.

Preferred are compounds of formula (1), wherein $R_1$ and $R_2$ independently of one another are hydrogen; or $C_1$-$C_{12}$alkyl.

Also referred are compounds of formula (1), wherein $R_3$ is $PO_3R_1R_2$, $COOR_6$; $COR_7$; or $SO_2R_6$; wherein $R_1$ and $R_2$, independently from each other are hydrogen; or unsubstituted or substituted $C_1$-$C_{12}$alkyl; and $R_6$ and $R_7$ independently from each other are unsubstituted or substituted $C_1$-$C_{18}$alkyl or $C_6$-$C_{20}$aryl.

Also referred are compounds of formula (1), wherein $R_4$ is unsubstituted $C_6$-$C_{20}$aryl; or $C_6$-$C_{20}$aryl which is substituted by at least one $C_1$-$C_{18}$alkyl, $C_1$-$C_{18}$alkoxy, hydroxy, mono- or di-$C_1$-$C_{18}$alkylamino or the radical of formula

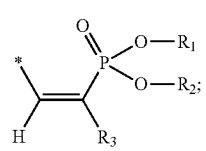

(1a)

wherein

R₁ and R₂ independently from each other are unsubstituted $C_1$-$C_{12}$alkyl;

R₃ is COOR₆; and

R₆ is $C_1$-$C_5$alkyl.

Also referred are compounds of formula (1), wherein R₅ is hydrogen; or $C_1$-$C_{20}$alkyl.

Most preferred are the compounds of formula

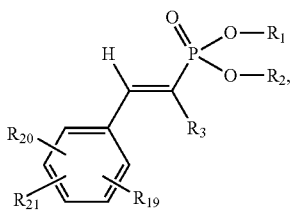

(2)

wherein

R₁ and R₂ independently from each other are $C_1$-$C_5$alkyl;

R₃ is —COOR₆; SO₂R₆; PO₃R₁R₂; COR₆; unsubstituted $C_6$-$C_{10}$aryl; or $C_6$-$C_{10}$aryl which is substituted by $C_1$-$C_5$alkyl or $C_1$-$C_5$alkoxy;

R₆ is $C_1$-$C_5$alkyl; or $C_6$-$C_{10}$aryl;

R₁₉, R₂₀ and R₂₁, independently from each other are hydrogen; $C_1$-$C_5$alkyl; $C_1$-$C_5$alkoxy; amino; $C_1$-$C_5$-dialkylamino; phenyl; or a radical of formula

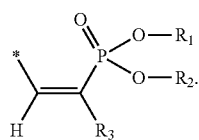

The compounds corresponding to formula (1) can be in their cis- or trans-form and/or can be in their protonated or deprotonated form.

$C_1$-$C_{12}$alkyl denotes straight-chain and branched hydrocarbon radicals, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl or dodecyl.

$C_1$-$C_{12}$alkoxy are straight-cain or branched radicals like methoxy, ethoxy, propoxy, butoxy, pentyloxy, hexyloxy, heptyloxy, octyloxy, isooctyloxy, nonyloxy, undecyloxy or dodecyloxy. $C_3$-$C_{12}$cycloalkyl is unsubstituted or by one or more than one $C_1$-$C_4$alkyl substituted $C_3$-$C_{12}$-cycloalkyl, for example cyclopropyl, cyclobutyl, cyclopentyl, cycloheptyl, cyclooctyl, cyclononyl, cyclodecyl, cycloundecyl, cyclodocecyl, 1-isopropyl-4-methyl-cyclohexyl (DL-menthyl) and most preferably cyclohexyl.

Hetero-$C_3$-$C_{12}$aryl is preferably pyridinyl, pyrimidinyl, triazinyl, pyrrolyl, furanyl, thiophenyl or chinolinyl.

$C_2$-$C_{20}$alkenyl is for example allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{20}$aryl is for example naphthyl and preferably phenyl or biphenyl.

Each alkyl can be linear or branched. Each alkyl or cycloalkyl can be saturated or unsaturated.

Each alkyl, cycloalkyl or alkoxy can preferably be substituted by one or more E and/or interrupted by one or more D.

Each aryl can be preferably substituted by G.

Each heteroaryl can be preferably substituted by G, $C_2$-$C_{18}$alkenyl, $C_2$-$C_{18}$alkynyl, $C_7$-$C_{25}$aralkyl, or CN.

Examples of phosphono compounds according to the present invention are listed in Table 1 below:

TABLE 1

Representatives of phosphonoesters according to the present invention.

P-01

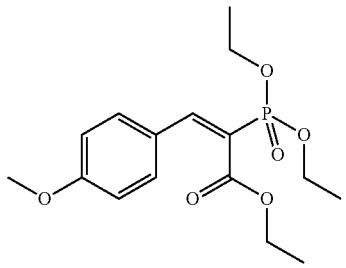 [SMILES: CCOC(=O)/C(=C\c1ccc(OC)cc1)P(=O)(OCC)OCC]

P-02

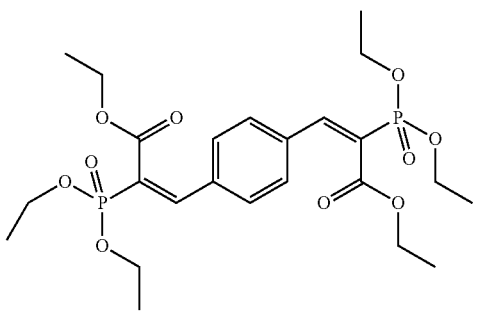 [SMILES: CCOC(=O)/C(=C\c1ccc(/C=C(\C(=O)OCC)P(=O)(OCC)OCC)cc1)P(=O)(OCC)OCC]

TABLE 1-continued
Representatives of phosphonoesters according to the present invention.
P-03
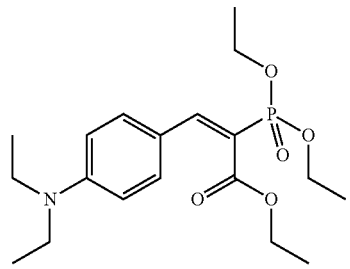 [SMILES: CCOC(=O)/C(=C\c1ccc(N(CC)CC)cc1)P(=O)(OCC)OCC]
P-04
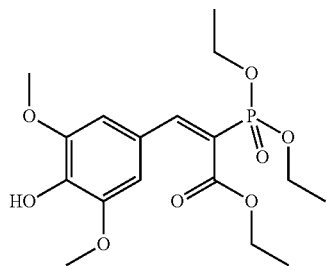 [SMILES: CCOC(=O)/C(=C\c1cc(OC)c(O)c(OC)c1)P(=O)(OCC)OCC]
P-05
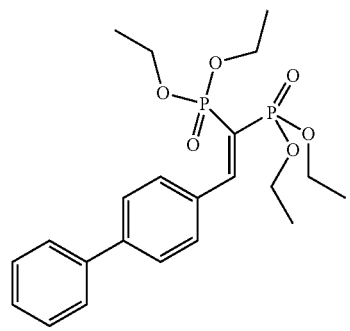 [SMILES: CCOP(=O)(OCC)C(=Cc1ccc(-c2ccccc2)cc1)P(=O)(OCC)OCC]
P-06
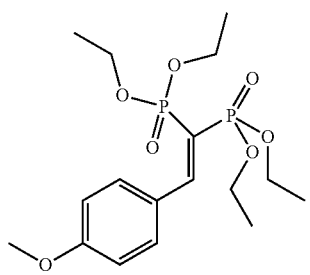 [SMILES: CCOP(=O)(OCC)C(=Cc1ccc(OC)cc1)P(=O)(OCC)OCC]
P-07
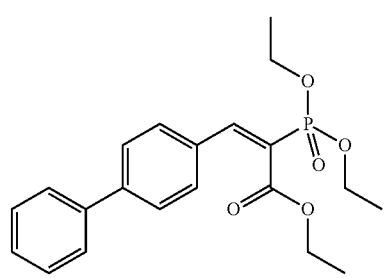 [SMILES: CCOC(=O)/C(=C\c1ccc(-c2ccccc2)cc1)P(=O)(OCC)OCC]

TABLE 1-continued
Representatives of phosphonoesters according to the present invention.
P-08
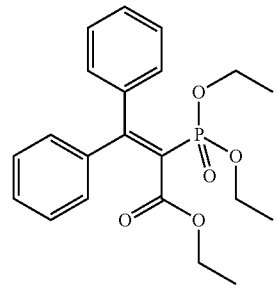 [SMILES: CCOC(=O)C(=C(c1ccccc1)c1ccccc1)P(=O)(OCC)OCC]
P-09
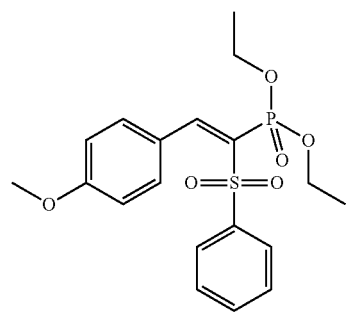 [SMILES: CCOP(=O)(OCC)/C(=C/c1ccc(OC)cc1)S(=O)(=O)c1ccccc1]
P-10
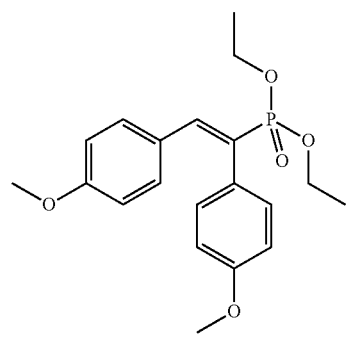 [SMILES: CCOP(=O)(OCC)/C(=C/c1ccc(OC)cc1)c1ccc(OC)cc1]
P-11
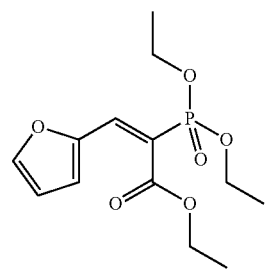 [SMILES: CCOC(=O)/C(=C\c1ccco1)P(=O)(OCC)OCC]
P-12
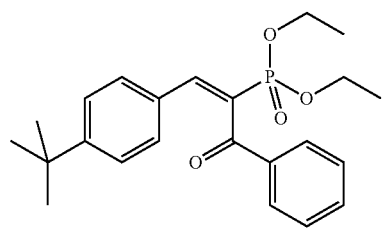 [SMILES: CCOP(=O)(OCC)/C(=C/c1ccc(C(C)(C)C)cc1)C(=O)c1ccccc1]

TABLE 1-continued
Representatives of phosphonoesters according to the present invention.
P-13
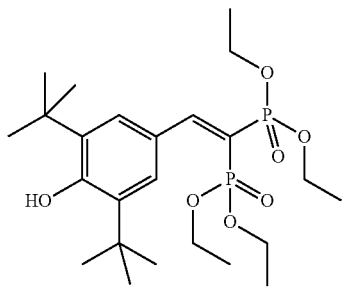 [SMILES: CCOP(=O)(OCC)C(=Cc1cc(C(C)(C)C)c(O)c(C(C)(C)C)c1)P(=O)(OCC)OCC]
P-14
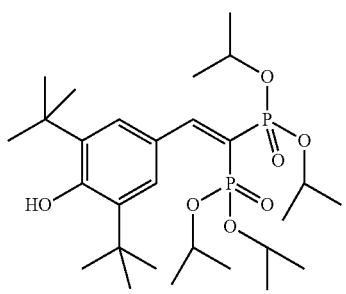 [SMILES: CC(C)OP(=O)(OC(C)C)C(=Cc1cc(C(C)(C)C)c(O)c(C(C)(C)C)c1)P(=O)(OC(C)C)OC(C)C]
P-15
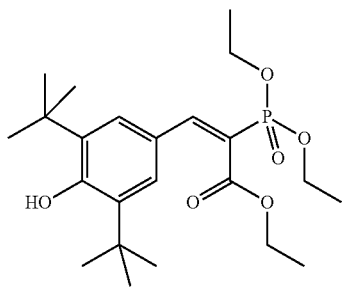 [SMILES: CCOC(=O)/C(=C\c1cc(C(C)(C)C)c(O)c(C(C)(C)C)c1)P(=O)(OCC)OCC]
P-16
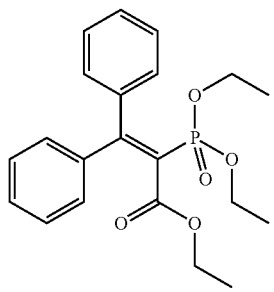 [SMILES: CCOC(=O)C(=C(c1ccccc1)c1ccccc1)P(=O)(OCC)OCC]
P-17
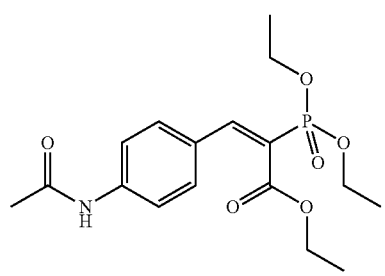 [SMILES: CCOC(=O)/C(=C\c1ccc(NC(C)=O)cc1)P(=O)(OCC)OCC]

TABLE 1-continued
Representatives of phosphonoesters according to the present invention.
P-18
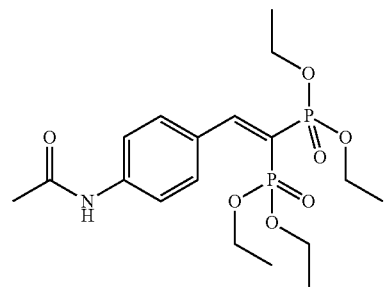 [SMILES: CCOP(=O)(OCC)C(=Cc1ccc(NC(C)=O)cc1)P(=O)(OCC)OCC]
P-19
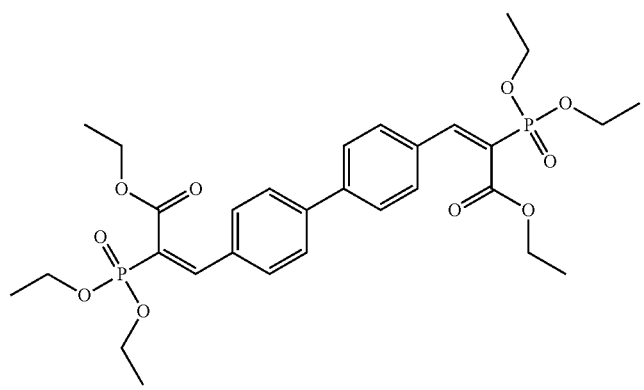 [SMILES: CCOC(=O)/C(=C\c1ccc(-c2ccc(/C=C(\C(=O)OCC)P(=O)(OCC)OCC)cc2)cc1)P(=O)(OCC)OCC]
P-20
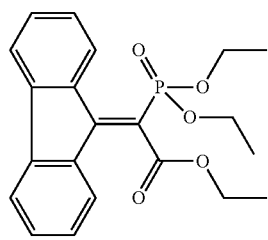 [SMILES: CCOC(=O)C(=C1c2ccccc2-c2ccccc21)P(=O)(OCC)OCC]
P-21
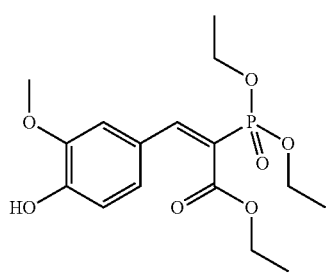 [SMILES: CCOC(=O)/C(=C\c1ccc(O)c(OC)c1)P(=O)(OCC)OCC]
P-22
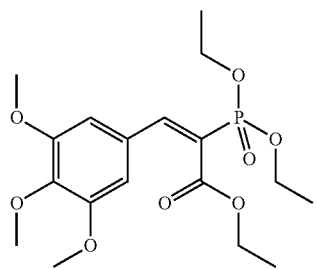 [SMILES: CCOC(=O)/C(=C\c1cc(OC)c(OC)c(OC)c1)P(=O)(OCC)OCC]

The phosphono UV absorbers can be prepared according to a procedure described by W. Lehnert in the journal "Tetrahedron" Vol. 30 (1974) on pages 301 to 305 by reacting a ketone or aldehyde of formula (1a) with a phosphono compound of general formula (1b) in the presence of titanium tetrachloride and an organic base, wherein the R groups are as defined above.

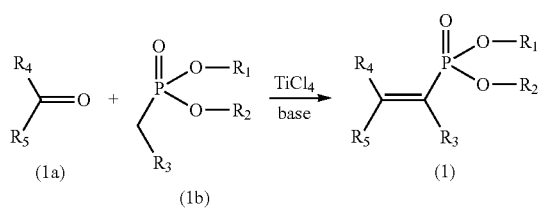

The reaction of a carbonyl compound of formula (1a) with a phosphonate of formula (1b) is preferably carried out in the absence of a solvent or in the presence of an organic solvent and more preferably in an ether solvent such as diethyl ether, dioxane, and tetrahydrofurane; a halogenated solvent like tetrachloromethane, chloroform or dichloromethane, an aromatic solvent such as toluene, xylene, mesitylene and benzene; a hydrocarbon solvent such as heptane, and petroleum ether, an ester solvent such as ethyl acetate, and methyl acetate; an alcohol solvent such a t-butanol, n-octanol-(1), and ethylene glycol; and an amide solvent such as dimethylformamide, dimethylacetamide, diethylacetamide, diethylpropionamide, and 1-methylpyrrolidone. Polar solvents such as dimethylsulfoxide are also suitable as well as mixtures of these solvents. Most preferably, the solvent is selected from tetrahydrofurane, dioxane, tetrachloromethane, chloroform and toluene and mixtures thereof.

The condensation reaction is facilitated by the use of titanium tetrachloride or another suitable Lewis acid. Examples for a Lewis acid are for example aluminium trichloride, potassium fluoride, titanium trichloride or zinc chloride.

In the preparation method of the present invention the methylene active compound of formula (1b) is reacted in the presence of an inorganic or organic base. Typical examples of an organic base are amines like N-methylmorpholine, morpholine, triethylamine, Hünig base, DBU (1,8-diazabicyclo [5.4.0]undec-7-ene), DBN (1,5-diazabicyclo[4.3.0]non-5-ene), p-dimethylaminopyridine and N,N,N',N'-tetramethylguanidine. Suitable bases are also alkoxides (e.g. sodium methoxide, sodium ethoxide, potassium t-butoxide). Inorganic bases like NaH, LiOH, sodium carbonate, potassium hydrogen carbonate and potassium carbonate are also suitable. Preferred is the use of an amine like N-methylmorpholine, triethylamine, DBU and the Hünig base.

The reaction temperature may be between –78° C. and the boiling point of the solvent used, but is preferably between –10° C. and 50° C., and more preferably between 0° C. and 20° C.

The molar ratio of the phosphono reagent of formula (1b) may be from 0.1 to 100 times, and preferably from 0.5 to 10 times, and more preferably from 1 to 2 times relating to the carbonyl derivative of formula (1a).

The molar ratio of titanium tetrachloride to the phosphono reagent of formula (1b) may be from 0.5 to 10 times, and preferably from 0.9 to 5 times, and more preferably from 1 to 2 times.

The amount (mass) of the solvent is from 0.5 to 100 times, and preferably from 1 to 50 times, and more preferably from 1 to 10 times as many as the mass of the carbonyl derivative of formula (1a).

The reaction end point may be confirmed, for example, through thin layer chromatography, gas chromatography or high performance liquid chromatography. After the reaction, the product, a phosphono derivatives of formula (1) may be obtained from the reaction mixture through ordinary product isolation by, for example, liquid-liquid separation, column chromatography, or crystallization by addition of a poor solvent to the reaction mixture, or by distillation.

The phosphono benzylidene compounds according to formula (1) are suitable especially as UV filters, that is to say for the protection of organic materials that are sensitive to ultraviolet light, especially human and animal skin and hair, against the action of UV radiation. Such compounds are accordingly suitable as light-protective agents in cosmetic, pharmaceutical and veterinary medicine preparations. Such compounds are preferably used in the dissolved state.

The invention accordingly relates also to a cosmetic preparation comprising at least one compound of formula (1), and cosmetically tolerable carriers or adjuvants.

The cosmetic preparation may also comprise, in addition to the UV absorber according to the invention, one or more further UV protective agents of the following substance classes:

1. p-aminobenzoic acid derivatives, for example 4-dimethylaminobenzoic acid 2-ethylhexyl ester;
2. salicylic acid derivatives, for example salicylic acid 2-ethylhexyl ester;
3. benzophenone derivatives, for example 2-hydroxy-4-methoxybenzophenone and its 5-sulfonic acid derivative;
4. dibenzoylmethane derivatives, for example 1-(4-tert-butylphenyl)-3-(4-methoxyphenyl)-propane-1,3-dione;
5. diphenylacrylates, for example 2-ethylhexyl 2-cyano-3,3-diphenylacrylate, and 3-(benzofuranyl)2-cyanoacrylate;
6. 3-imidazol-4-ylacrylic acid and esters;
7. benzofuran derivatives, especially 2-(p-aminophenyl)benzofuran derivatives, described in EP-A-582 189, U.S. Pat. Nos. 5,338,539, 5,518,713 and EP-A-613 893;
8. polymeric UV absorbers, for example the benzylidene malonate derivatives described in EP-A-709 080;
9. cinnamic acid derivatives, for example the 4-methoxycinnamic acid 2-ethylhexyl ester and isoamyl ester or cinnamic acid derivatives disclosed in U.S. Pat. No. 5,601,811 and WO 97/00851;
10. camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
11. hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxyl]-phenyl}-6-(4-methoxyphenyl)-1,3,5-triazine; 2,4-bis{[4-(2-ethylhexyloxy)-2-hydroxyl]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxyl]-phenyl}-6-(4-methoxyphenyl)-1,3,5-triazine; 2,4-bis{[4-(2"-methylpropenyloxy)-2-hydroxyl]-phenyl}-6-(4-methoxyphenyl)-1,3,5-triazine; 2,4-bis{[4-(1',1',1',3',5',5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxypropyloxy)-2-hydroxyl]-phenyl}-6-[4-ethylcarboxyyphenylamino]-1,3,5-triazine;

12. benzotriazole compounds, for example 2,2'-methylene-bis(6-(2H-benzotriazol-2-yl)-4-(1,1,3,3-tetramethylbutyl)-phenol

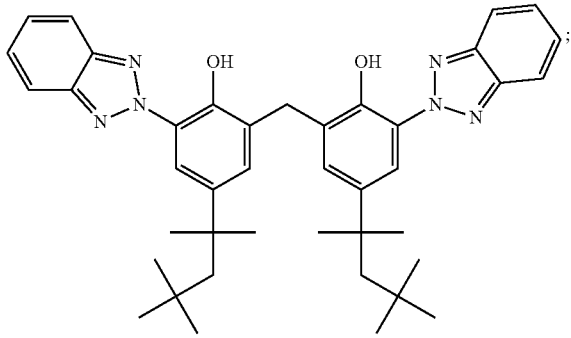 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]

13. trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517104, EP-A-507691, WO 93/17002 and EP-A-570838;
14. 2-phenylbenzimidazole-5-sulfonic acid and salts thereof;
15. menthyl o-aminobenzoate;
16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table:

| INCI | Chemical Name | CAS No. |
|---|---|---|
| 3-BENZYLIDENE CAMPHOR | 1,7,7-trimethyl-3-(phenylmethylene)-bicyclo[2.2.1]heptan-2-one | 15087-24-8 |
| 4-METHYLBENZYLIDENE CAMPHOR | (+/−)-1,7,7-trimethyl-3-[(4-methylphenyl)-methylene]bicyclo[2.2.1]heptan-2-one | 36861-47-9 |
| BENZOPHENONE-10 | 2-hydroxy-4-methoxyphenyl)-(4-methylphenyl)methanone | 1641-17-4 |
| BENZOPHENONE-1 | 2,4-dihydroxybenzophenone | 131-56-6 |
| BENZOPHENONE-2 | 2,2',4,4'-tetrahydroxybenzophenone | 131-55-5 |
| BENZOPHENONE-3 | 2-hydroxy-4-methoxybenzophenone | 131-57-7 |
| BENZOPHENONE-4 | 2-hydroxy-4-methoxybenzophenone-5-sulfonic acid | 4065-45-6 |
| BENZOPHENONE-6 | 2,2'-dihydroxy-4,4'-dimethoxybenzophenone | 131-54-4 |
| BENZOPHENONE-8 | 2,2'-dihydroxy-4-methoxybenzophenone | 131-53-3 |
| BENZYLIDENE CAMPHOR SULFONIC ACID | alpha-(2-oxoborn-3-ylidene)-toluene-4-sulfonic acid and its salts | 56039-58-8 |
| BUTYL METHOXY-DIBENZOYLMETHANE | 1-[4-(1,1-dimethylethyl)phenyl]-3-(4-methoxyphenyl)propane-1,3-dione | 70356-09-1 |
| CAMPHOR BENZALKONIUM METHOSULFATE | methyl N,N,N-trimethyl-4-[(4,7,7-trimethyl-3-oxobicyclo[2,2,1]hept-2-ylidene)methyl]-anilinium sulfate | 52793-97- |
| CINOXATE | 2-ethoxyethyl p-methoxycinnamate | 104-28-9 |
| DEA-METHOXYCINNAMATE | diethanolamine salt of p-methoxy-hydrocinnamate | 56265-46-4 |
| DIISOPROPYL METHYL CINNAMATE | 2-propenoic acid, 3-[2,4-bis(1-methylethyl)phenyl]-, methyl ester | 32580-71-5 |
| DIPROPYLENE GLYCOL SALICYLATE | dipropylene glycol salicylate | 7491-14-7 |
| ETHYL DIHYDROXYPROPYL PABA | ethyl 4-bis(2-hydroxypropyl)-amino-benzoate | 58882-17-0 |
| ETHYL DIISOPROPYLCINNAMATE | ethyl 3-[2,4-bis(1-methylethyl)phenyl]acrylate | 32580-72-6 |
| ETHYL METHOXYCINNAMATE | ethyl p-methoxycinnamate | 1929-30-2 |
| GLYCERYL OCTANOATE DIMETHOXYCINNAMATE | | |
| GLYCERYL PABA | glyceryl 1-(4-aminobenzoate) | 136-44-7 |
| HOMOSALATE | 3,3,5-trimethylcyclohexyl-2-hydroxy-benzoate | 118-56-9 |
| ISOAMYL p-METHOXY-CINNAMATE | isopentyl p-methoxycinnamate | 71617-10-2 |
| ISOPROPYL DIBENZOYLMETHANE | 1-[4-(1-methylethyl)phenyl]-3-phenyl-propane-1,3-dione | 63250-25-9 |
| ISOPROPYL METHOXYCINNAMATE | isopropyl p-methoxycinnamate | 5466-76-2 |
| LAWSONE | 2-hydroxy-1,4-naphthoquinone | 83-72-7 |
| MENTHYL ANTHRANILATE | menthyl o-aminobenzoate | 134-09-8 |
| MENTHYL SALICYLATE | menthyl salicylate | 89-46-3 |
| OCTOCRYLENE | 2-ethylhexyl 2-cyano-3,3-diphenyl acrylate | 6197-30-4 |
| ETHYLHEXYL DIMETHYL PABA | 2-ethylhexyl 4-(dimethylamino)benzoate | 21245-02-3 |
| ETHYLHEXYL METHOXYCINNAMATE | 2-ethylhexyl 4-methoxycinnamate | 5466-77-3 |
| ETHYLHEXYL SALICYLATE | 2-ethylhexyl salicylate | 118-60-5 |

-continued

| INCI | Chemical Name | CAS No. |
|---|---|---|
| ETHYLHEXYL TRIAZONE | benzoic acid, 4,4',4''-(1,3,5-triazine-2,4,6-triyltriimino)tris-, tris(2-ethylhexyl) ester; 2,4,6-trianilino-(p-carbo-2'-ethylhexyl-1'-oxy)-1,3,5-triazine | 88122-99-0 |
| PABA | 4-aminobenzoic acid | 150-13-0 |
| PEG-25 PABA | benzoic acid, 4-amino-, ethyl ester, polymer with oxirane | 113010-52-9 |
| PENTYL DIMETHYL PABA | amyl dimethyl PABA | 14779-78-3 |
| PHENYLBENZIMIDAZOLE SULFONIC ACID | 2-phenyl-1H-benzimidazole-5-sulfonic acid | 27503-81-7 |
| POLYACRYLAMIDOMETHYL BENZYLIDENE CAMPHOR | | 113783-61-2 |
| TEA-SALICYLATE | triethanolamine salicylate | 2174-16-5 |
| TEREPHTHALYLIDENE DICAMPHOR SULFONIC ACID | 3,3'-(1,4-phenylenedimethylene)bis[7,7-dimethyl-2-oxo-bicyclo[2.2.1]heptane-1-methanesulfonic acid] | 90457-82-2 |
| TITANIUM DIOXIDE | titanium dioxide | 13463-67-7 |
| DIGALLOYL TRIOLEATE | digalloyl trioleate | 17048-39-4 |
| ZINC OXIDE | zinc oxide | 1314-13-2 |
| Methylene bis-benzotriazolyl tetramethylbutylphenol | 2,2'-methylene-bis[6-(2H-benzotriazol-2-yl)-4-(1,1,3,3-tetramethylbutyl)-phenol] | 103597-45-1 |
| Bis-ethylhexyloxyphenol methoxyphenyltriazine | 2,4-bis{[4-(2-ethylhexyloxy)-2-hydroxy]-phenyl}-6-(4-methoxyphenyl)-(1,3,5)-triazine | 187393-00-6 |
| BISIMIDAZYLATE | 1H-benzimidazole-4,6-disulfonic acid, 2,2'-(1,4-phenylene)bis-, disodium salt | 180898-37-7 |
| DIETHYLHEXYL BUTAMIDO TRIAZONE | benzoic acid, 4,4'-[[6-[[4-[[(1,1-dimethylethyl)-amino]carbonyl]phenyl]amino]-1,3,5-triazine-2,4-diyl]diimino]bis-, bis(2-ethyl-hexyl) ester | 154702-15-5 |
| DROMETRIZOLE TRISILOXANE | phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| BENZYLIDENE MALONATE POLYSILOXANE | alpha-(trimethylsilyl)-omega-(trimethyl-silyl-oxy)poly[oxy(dimethyl)silylene]-co-[oxy(methyl)(2-{p-[2,2-bis(ethoxycarbonyl)vinyl]-phenoxy}-1-methyleneethyl)silylene]-co-[oxy(methyl)(2-{p-[2,2-bis(ethoxycarbonyl)-vinyl]phenoxy}prop-1-enyl)silylene] | 207574-74-1 |
| | 2-(4-diethylamino-2-hydroxybenzoyl)-benzoic hexyl ester | 302776-68-7 |

Each of the above-mentioned light-protective agents, especially the light-protective agents in the above Table indicated as being preferred, can be used in admixture with the UV absorbers according to the invention. It will be understood in that connection that, in addition to the UV absorbers according to the invention, it is also possible for more than one of the additional light-protective agents to be used, for example, two, three, four, five or six further light-protective agents. Preference is given to the use of mixing ratios of UV absorbers according to the invention/further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably of approximately 50:50. Such mixtures can be used, inter alia, to improve solubility or to increase UV absorption.

Appropriate mixtures can be used especially advantageously in a cosmetic composition according to the invention.

Suitable new UV filters are listed in Table 1 (compounds P-01-P-14).

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The described cosmetic or pharmaceutical preparations are distinguished by excellent protection of human skin against the damaging effect of sunlight.

The following mixtures of soluble UV filters (Table 2) can be mixed together with the benzylidene compounds according to the present invention:

TABLE 2

List of oil soluble organic UV filter combinations

| Combination Nr. | BP3 | BP4 | 3BC | BEMT | BMBM | DBT | DTS | EHT | MBC | PAMBC |
|---|---|---|---|---|---|---|---|---|---|---|
| UV SOL 1 | x | | | | | | | | | |
| UV SOL 2 | | x | | | | | | | | |
| UV SOL 3 | | | x | | | | | | | |
| UV SOL 4 | | | | x | | | | | | |
| UV SOL 5 | | | | | x | | | | | |

TABLE 2-continued

List of oil soluble organic UV filter combinations

| | 1 | 2 | 3 | 4 | 5 | 6 | 7 | 8 | 9 | 10 |
|---|---|---|---|---|---|---|---|---|---|---|
| UV SOL 6 | | | | | | x | | | | |
| UV SOL 7 | | | | | | | x | | | |
| UV SOL 8 | | | | | | | | x | | |
| UV SOL 9 | | | | | | | | | x | |
| UV SOL 10 | | | | | | | | | | x |
| UV SOL 11 | x | x | | | | | | | | |
| UV SOL 12 | x | | x | | | | | | | |
| UV SOL 13 | x | | | x | | | | | | |
| UV SOL 14 | x | | | | x | | | | | |
| UV SOL 15 | x | | | | | x | | | | |
| UV SOL 16 | x | | | | | | x | | | |
| UV SOL 17 | x | | | | | | | x | | |
| UV SOL 18 | x | | | | | | | | x | |
| UV SOL 19 | x | | | | | | | | | x |
| UV SOL 20 | | x | x | | | | | | | |
| UV SOL 21 | | x | | x | | | | | | |
| UV SOL 22 | | x | | | x | | | | | |
| UV SOL 23 | | x | | | | x | | | | |
| UV SOL 24 | | x | | | | | x | | | |
| UV SOL 25 | | x | | | | | | x | | |
| UV SOL 26 | | x | | | | | | | x | |
| UV SOL 27 | | x | | | | | | | | x |
| UV SOL 28 | | | x | x | | | | | | |
| UV SOL 29 | | | x | | x | | | | | |
| UV SOL 30 | | | x | | | x | | | | |
| UV SOL 31 | | | x | | | | x | | | |
| UV SOL 32 | | | x | | | | | x | | |
| UV SOL 33 | | | x | | | | | | x | |
| UV SOL 34 | | | x | | | | | | | x |
| UV SOL 35 | | | | x | x | | | | | |
| UV SOL 36 | | | | x | | x | | | | |
| UV SOL 37 | | | | x | | | x | | | |
| UV SOL 38 | | | | x | | | | x | | |
| UV SOL 39 | | | | x | | | | | x | |
| UV SOL 40 | | | | x | | | | | | x |
| UV SOL 41 | | | | | x | x | | | | |
| UV SOL 42 | | | | | x | | x | | | |
| UV SOL 43 | | | | | x | | | x | | |
| UV SOL 44 | | | | | x | | | | x | |
| UV SOL 45 | | | | | x | | | | | x |
| UV SOL 46 | | | | | | x | x | | | |
| UV SOL 47 | | | | | | x | | x | | |
| UV SOL 48 | | | | | | x | | | x | |
| UV SOL 49 | | | | | | x | | | | x |
| UV SOL 50 | | | | | | | x | x | | |
| UV SOL 51 | | | | | | | x | | x | |
| UV SOL 52 | | | | | | | x | | | x |
| UV SOL 53 | | | | | | | | x | x | |
| UV SOL 54 | | | | | | | | x | | x |
| UV SOL 55 | | | | | | | | | x | x |
| UV SOL 56 | x | x | x | | | | | | | |
| UV SOL 57 | x | x | | x | | | | | | |
| UV SOL 58 | x | x | | | x | | | | | |
| UV SOL 59 | x | x | | | | x | | | | |
| UV SOL 60 | x | x | | | | | x | | | |
| UV SOL 61 | x | x | | | | | | x | | |
| UV SOL 62 | x | x | | | | | | | x | |
| UV SOL 63 | x | x | | | | | | | | x |
| UV SOL 64 | x | | x | x | | | | | | |
| UV SOL 65 | x | | x | | x | | | | | |
| UV SOL 66 | x | | x | | | x | | | | |
| UV SOL 67 | x | | x | | | | x | | | |
| UV SOL 68 | x | | x | | | | | x | | |
| UV SOL 69 | x | | x | | | | | | x | |
| UV SOL 70 | x | | x | | | | | | | x |
| UV SOL 71 | x | | | x | x | | | | | |
| UV SOL 72 | x | | | x | | x | | | | |
| UV SOL 73 | x | | | x | | | x | | | |
| UV SOL 74 | x | | | x | | | | x | | |
| UV SOL 75 | x | | | x | | | | | x | |
| UV SOL 76 | x | | | x | | | | | | x |
| UV SOL 77 | x | | | | x | x | | | | |
| UV SOL 78 | x | | | | x | | x | | | |
| UV SOL 79 | x | | | | x | | | x | | |
| UV SOL 80 | x | | | | x | | | | x | |
| UV SOL 81 | x | | | | x | | | | | x |
| UV SOL 82 | x | | | | | x | x | | | |
| UV SOL 83 | x | | | | | x | | x | | |

TABLE 2-continued

List of oil soluble organic UV filter combinations

| | 1 | 2 | 3 | 4 | 5 | 6 | 7 |
|---|---|---|---|---|---|---|---|
| UV SOL 84 | x | | | | x | | x | |
| UV SOL 85 | x | | | | | x | | x |
| UV SOL 86 | x | | | | | x | x | |
| UV SOL 87 | x | | | | | x | | x |
| UV SOL 88 | x | | | | | x | | | x |
| UV SOL 89 | x | | | | | | x | x |
| UV SOL 90 | x | | | | | | x | | x |
| UV SOL 91 | x | | | | | | | x | x |
| UV SOL 92 | | x | x | x | | | | |
| UV SOL 93 | | x | x | | x | | | |
| UV SOL 94 | | x | x | | | x | | |
| UV SOL 95 | | x | x | | | | x | |
| UV SOL 96 | | x | x | | | | | x |
| UV SOL 97 | | x | x | | | | | x |
| UV SOL 98 | | x | x | | | | | | x |
| UV SOL 99 | | x | | x | x | | | |
| UV SOL 100 | | x | | x | | x | | |
| UV SOL 101 | | x | | x | | | x | |
| UV SOL 102 | | x | | x | | | x | |
| UV SOL 103 | | x | | x | | | | x |
| UV SOL 104 | | x | | x | | | | | x |
| UV SOL 105 | | x | | | x | x | | |
| UV SOL 106 | | x | | | x | | x | |
| UV SOL 107 | | x | | | x | | x | |
| UV SOL 108 | | x | | | x | | | x |
| UV SOL 109 | | x | | | x | | | | x |
| UV SOL 110 | | x | | | | x | x | |
| UV SOL 111 | | x | | | | x | x | |
| UV SOL 112 | | x | | | | x | | x |
| UV SOL 113 | | x | | | | x | | | x |
| UV SOL 114 | | x | | | | | x | x |
| UV SOL 115 | | x | | | | | x | x |
| UV SOL 116 | | x | | | | | x | | x |
| UV SOL 117 | | x | | | | | | x | x |
| UV SOL 118 | | x | | | | | | x | x |
| UV SOL 119 | | x | | | | | | x | x |
| UV SOL 120 | | | x | x | x | | | |
| UV SOL 121 | | | x | x | | x | | |
| UV SOL 122 | | | x | x | | | x | |
| UV SOL 123 | | | x | x | | | x | |
| UV SOL 124 | | | x | x | | | | x |
| UV SOL 125 | | | x | x | | | | | x |
| UV SOL 126 | | | x | | x | x | | |
| UV SOL 127 | | | x | | x | | x | |
| UV SOL 128 | | | x | | x | | x | |
| UV SOL 129 | | | x | | x | | | x |
| UV SOL 130 | | | x | | x | | | | x |
| UV SOL 131 | | | x | | | x | x | |
| UV SOL 132 | | | x | | | x | x | |
| UV SOL 133 | | | x | | | x | | x |
| UV SOL 134 | | | x | | | x | | | x |
| UV SOL 135 | | | x | | | | x | x |
| UV SOL 136 | | | x | | | | x | x |
| UV SOL 137 | | | x | | | | x | | x |
| UV SOL 138 | | | x | | | | | x | x |
| UV SOL 139 | | | x | | | | | x | x |
| UV SOL 140 | | | x | | | | | x | x |
| UV SOL 141 | | | | x | x | x | | |
| UV SOL 142 | | | | x | x | | x | |
| UV SOL 143 | | | | x | x | | x | |
| UV SOL 144 | | | | x | x | | | x |
| UV SOL 145 | | | | x | x | | | | x |
| UV SOL 146 | | | | x | | x | x | |
| UV SOL 147 | | | | x | | x | x | |
| UV SOL 148 | | | | x | | x | | x |
| UV SOL 149 | | | | x | | x | | | x |
| UV SOL 150 | | | | x | | | x | x |
| UV SOL 151 | | | | x | | | x | x |
| UV SOL 152 | | | | x | | | x | | x |
| UV SOL 153 | | | | x | | | | x | x |
| UV SOL 154 | | | | x | | | | x | x |
| UV SOL 155 | | | | x | | | | x | x |
| UV SOL 156 | | | | | x | x | x | |
| UV SOL 157 | | | | | x | x | x | |
| UV SOL 158 | | | | | x | x | | x |
| UV SOL 159 | | | | | x | x | | | x |
| UV SOL 160 | | | | | x | | x | x |
| UV SOL 161 | | | | | x | | x | x |

TABLE 2-continued

List of oil soluble organic UV filter combinations

| | | | | | | | | |
|---|---|---|---|---|---|---|---|---|
| UV SOL 162 | | | | x | | x | | x |
| UV SOL 163 | | | | x | | | x | x |
| UV SOL 164 | | | | x | | | x | | x |
| UV SOL 165 | | | | x | | | | x | x |
| UV SOL 166 | | | | | x | x | x | |
| UV SOL 167 | | | | | x | x | | x |
| UV SOL 168 | | | | | x | x | | | x |
| UV SOL 169 | | | | | x | | x | x |
| UV SOL 170 | | | | | x | | x | | x |
| UV SOL 171 | | | | | x | | | x | x |
| UV SOL 172 | | | | | | x | x | x |
| UV SOL 173 | | | | | | x | x | | x |
| UV SOL 174 | | | | | | x | | x | x |
| UV SOL 175 | | | | | | | x | x | x |
| UV SOL 176 | x | x | x | x | | | | |
| UV SOL 177 | x | x | x | | x | | | |
| UV SOL 178 | x | x | x | | | x | | |
| UV SOL 179 | x | x | x | | | x | | |
| UV SOL 180 | x | x | x | | | | x | |
| UV SOL 181 | x | x | x | | | | | x |
| UV SOL 182 | x | | x | x | x | | | | x |
| UV SOL 183 | x | | x | x | | x | | |
| UV SOL 184 | x | | x | x | | | x | |
| UV SOL 185 | x | | x | x | | | | x |
| UV SOL 186 | x | | x | x | | | | | x |
| UV SOL 187 | x | | x | | | | | | x |
| UV SOL 188 | x | | | x | x | x | | |
| UV SOL 189 | x | | | x | x | | x | |
| UV SOL 190 | x | | | x | x | | | x |
| UV SOL 191 | x | | | x | x | | | | x |
| UV SOL 192 | x | | | x | x | | | | x |
| UV SOL 193 | x | | | x | x | x | | |
| UV SOL 194 | x | | | x | x | | x | |
| UV SOL 195 | x | | | x | x | | | x |
| UV SOL 196 | x | | | x | x | | | | x |
| UV SOL 197 | x | | | | x | x | x | |
| UV SOL 198 | x | | | | x | x | | x |
| UV SOL 199 | x | | | | x | x | | | x |
| UV SOL 200 | x | | | | | x | x | x |
| UV SOL 201 | x | | | | | x | x | | x |
| UV SOL 202 | x | | | | | | x | x | x |
| UV SOL 203 | | x | x | x | x | | | |
| UV SOL 204 | | x | x | x | | x | | |
| UV SOL 205 | | x | x | x | | | x | |
| UV SOL 206 | | x | x | x | | | | x |
| UV SOL 207 | | x | x | x | | | | | x |
| UV SOL 208 | | x | x | x | | | | | x |
| UV SOL 209 | | x | | x | x | | x | |
| UV SOL 210 | | x | | x | x | | | x |
| UV SOL 211 | | x | | x | x | | | | x |
| UV SOL 212 | | x | | x | x | | | | x |
| UV SOL 213 | | x | | | x | x | x | |
| UV SOL 214 | | x | | | x | x | | x |
| UV SOL 215 | | x | | | x | x | | | x |
| UV SOL 216 | | x | | | x | x | | | x |
| UV SOL 217 | | x | | | x | | x | x |
| UV SOL 218 | | x | | | x | | x | | x |
| UV SOL 219 | | x | | | x | | | x | x |
| UV SOL 220 | | x | | | | x | x | x |
| UV SOL 221 | | x | | | | x | x | | x |
| UV SOL 222 | | x | | | | | x | x | x |
| UV SOL 223 | | | x | x | x | x | | |
| UV SOL 224 | | | x | x | x | | x | |
| UV SOL 225 | | | x | x | x | | | x |
| UV SOL 226 | | | x | x | x | | | x |
| UV SOL 227 | | | x | x | x | | | | x |
| UV SOL 228 | | | x | | x | x | x | |
| UV SOL 229 | | | x | | x | x | | x |
| UV SOL 230 | | | x | | x | x | | | x |
| UV SOL 231 | | | x | | | x | x | x |
| UV SOL 232 | | | x | | | x | x | | x |
| UV SOL 233 | | | x | | | x | x | | x |
| UV SOL 234 | | | x | | | | x | x | x |
| UV SOL 235 | | | x | | | | x | x | x |
| UV SOL 236 | | | x | | | | | x | x | x |
| UV SOL 237 | | | | x | x | x | x | |
| UV SOL 238 | | | | x | x | x | | x |
| UV SOL 239 | | | | x | x | x | | x |

TABLE 2-continued

List of oil soluble organic UV filter combinations

| | | | | | | | | |
|---|---|---|---|---|---|---|---|---|
| UV SOL 240 | | x | x | x | | | x | x |
| UV SOL 241 | | x | | x | x | | x | |
| UV SOL 242 | | x | | x | x | | | x |
| UV SOL 243 | | x | | | x | x | x | |
| UV SOL 244 | | x | | | x | x | | x |
| UV SOL 245 | | x | | | | x | x | x |
| UV SOL 246 | | | x | x | x | x | | |
| UV SOL 247 | | | x | x | x | | x | |
| UV SOL 248 | | | x | x | x | | | x |
| UV SOL 249 | | | x | | x | x | | x |
| UV SOL 250 | | | x | | | x | x | x |
| UV SOL 251 | | | | x | x | x | x | |
| UV SOL 252 | | | | x | x | x | | x |
| UV SOL 253 | | | | x | x | x | x | x |

Table 2 Abbreviations

| | | |
|---|---|---|
| BP3 | Benzophenone 3 | 131-57-7 |
| BP4 | Benzophenone-4 | 4065-45-6 |
| 3BC | 3-Benzydilene Camphor | 15087-24-8 |
| BEMT | Bis-Ethylhexyloxyphenol Methoxyphenyl Triazine | 103597-45-1 |
| BMBM | Butyl Methoxydibenzoylmethane | 70356-09-1 |
| DBT | Diethylhexyl Butamido Triazone | 154702-15-5 |
| DTS | Drometrizole Trisiloxane | 155633-54-8 |
| EHT | Ethylhexyl Triazone | 88122-99-0 |
| MBC | 4-Methylbenzylidene Camphor | 36861-47-9 |
| PAMBC | Polyacrylamido Methylbenzylidene Camphor | 147897-12-9 |

The following mixtures of oil miscible organic UV filters (Table 3) can be mixed together with the benzylidene compounds according to the present invention:

TABLE 3

List of oil miscible organic UV filter combinations

| Combination Nr. | DHHB | EHDP | EHMC | EHS | HMS | IMC | OCR | PS15 |
|---|---|---|---|---|---|---|---|---|
| UV LIQ 1 | x | | | | | | | |
| UV LIQ 2 | | x | | | | | | |
| UV LIQ 3 | | | x | | | | | |
| UV LIQ 4 | | | | x | | | | |
| UV LIQ 5 | | | | | x | | | |
| UV LIQ 6 | | | | | | x | | |
| UV LIQ 7 | | | | | | | x | |
| UV LIQ 8 | | | | | | | | x |
| UV LIQ 9 | x | x | | | | | | |
| UV LIQ 10 | x | | x | | | | | |
| UV LIQ 11 | x | | | x | | | | |
| UV LIQ 12 | x | | | | x | | | |
| UV LIQ 13 | x | | | | | x | | |
| UV LIQ 14 | x | | | | | | x | |
| UV LIQ 15 | x | | | | | | | x |
| UV LIQ 16 | | x | x | | | | | |
| UV LIQ 17 | | x | | x | | | | |
| UV LIQ 18 | | x | | | x | | | |
| UV LIQ 19 | | x | | | | x | | |
| UV LIQ 20 | | x | | | | | x | |
| UV LIQ 21 | | x | | | | | | x |
| UV LIQ 22 | | | x | x | | | | |
| UV LIQ 23 | | | x | | x | | | |
| UV LIQ 24 | | | x | | | x | | |
| UV LIQ 25 | | | x | | | | x | |
| UV LIQ 26 | | | x | | | | | x |
| UV LIQ 27 | | | | x | x | | | |
| UV LIQ 28 | | | | x | | x | | |
| UV LIQ 29 | | | | x | | | x | |
| UV LIQ 30 | | | | x | | | | x |
| UV LIQ 31 | | | | | x | x | | |
| UV LIQ 32 | | | | | x | | x | |
| UV LIQ 33 | | | | | x | | | x |
| UV LIQ 34 | | | | | | x | x | |
| UV LIQ 35 | | | | | | x | | x |

TABLE 3-continued

List of oil miscible organic UV filter combinations

| | | | | | | | | |
|---|---|---|---|---|---|---|---|---|
| UV LIQ 36 | | | | | | | x | x |
| UV LIQ 37 | x | x | x | | | | | |
| UV LIQ 38 | x | x | | x | | | | |
| UV LIQ 39 | x | x | | | x | | | |
| UV LIQ 40 | x | x | | | | x | | |
| UV LIQ 41 | x | x | | | | | x | |
| UV LIQ 42 | x | x | | | | | | x |
| UV LIQ 43 | x | | x | x | | | | |
| UV LIQ 44 | x | | x | | x | | | |
| UV LIQ 45 | x | | x | | | x | | |
| UV LIQ 46 | x | | x | | | | x | |
| UV LIQ 47 | x | | x | | | | | x |
| UV LIQ 48 | x | | | x | x | | | |
| UV LIQ 49 | x | | | x | | x | | |
| UV LIQ 50 | x | | | x | | | x | |
| UV LIQ 51 | x | | | x | | | | x |
| UV LIQ 52 | x | | | | x | x | | |
| UV LIQ 53 | x | | | | x | | x | |
| UV LIQ 54 | x | | | | x | | | x |
| UV LIQ 55 | x | | | | | x | x | |
| UV LIQ 56 | x | | | | | x | | x |
| UV LIQ 57 | x | | | | | | x | x |
| UV LIQ 58 | | x | x | x | | | | |
| UV LIQ 59 | | x | x | | x | | | |
| UV LIQ 60 | | x | x | | | x | | |
| UV LIQ 61 | | x | x | | | | x | |
| UV LIQ 62 | | x | x | | | | | x |
| UV LIQ 63 | | x | | x | x | | | |
| UV LIQ 64 | | x | | x | | x | | |
| UV LIQ 65 | | x | | x | | | x | |
| UV LIQ 66 | | x | | x | | | | x |
| UV LIQ 67 | | x | | | x | x | | |
| UV LIQ 68 | | x | | | x | | x | |
| UV LIQ 69 | | x | | | x | | | x |
| UV LIQ 70 | | x | | | | x | x | |
| UV LIQ 71 | | x | | | | x | | x |
| UV LIQ 72 | | x | | | | | x | x |
| UV LIQ 73 | | | x | x | x | | | |
| UV LIQ 74 | | | x | x | | x | | |
| UV LIQ 75 | | | x | x | | | x | |
| UV LIQ 76 | | | x | x | | | | x |
| UV LIQ 77 | | | x | | x | x | | |
| UV LIQ 78 | | | x | | x | | x | |
| UV LIQ 79 | | | x | | x | | | x |
| UV LIQ 80 | | | x | | | x | x | |
| UV LIQ 81 | | | x | | | x | | x |
| UV LIQ 82 | | | x | | | | x | x |
| UV LIQ 83 | | | | x | x | x | | |
| UV LIQ 84 | | | | x | x | | x | |
| UV LIQ 85 | | | | x | x | | | x |
| UV LIQ 86 | | | | x | | x | x | |
| UV LIQ 87 | | | | x | | x | | x |
| UV LIQ 88 | | | | x | | | x | x |
| UV LIQ 89 | | | | | x | x | x | |
| UV LIQ 90 | | | | | x | x | | x |
| UV LIQ 91 | | | | | x | | x | x |
| UV LIQ 92 | | | | | | x | x | x |
| UV LIQ 93 | x | x | x | x | | | | |
| UV LIQ 94 | x | x | x | | x | | | |
| UV LIQ 95 | x | x | x | | | x | | |
| UV LIQ 96 | x | x | x | | | | x | |
| UV LIQ 97 | x | x | x | | | | | x |
| UV LIQ 98 | x | x | | x | x | | | |
| UV LIQ 99 | x | x | | x | | x | | |
| UV LIQ 100 | x | x | | x | | | x | |
| UV LIQ 101 | x | | | | x | x | x | |
| UV LIQ 102 | x | | | | x | x | | x |
| UV LIQ 103 | x | | | | x | | x | x |
| UV LIQ 104 | x | | | | | x | x | x |
| UV LIQ 105 | x | | | | | x | | x |
| UV LIQ 106 | x | | | | | | x | x |
| UV LIQ 107 | | x | x | x | x | | | |
| UV LIQ 108 | | x | x | x | | x | | |
| UV LIQ 109 | | x | x | x | | | x | |
| UV LIQ 110 | | x | x | x | | | | x |
| UV LIQ 111 | | x | x | | x | x | | |
| UV LIQ 112 | | x | x | | x | | x | |
| UV LIQ 113 | | x | | | x | x | x | |

TABLE 3-continued

List of oil miscible organic UV filter combinations

| | | | | | | | |
|---|---|---|---|---|---|---|---|
| UV LIQ 114 | x | | | x | x | | x |
| UV LIQ 115 | x | | | | x | x | x |
| UV LIQ 116 | | x | x | x | x | | |
| UV LIQ 117 | | x | x | x | | x | |
| UV LIQ 118 | | x | x | x | | | x |
| UV LIQ 119 | | x | | x | x | | x |
| UV LIQ 120 | | x | | | x | x | x |
| UV LIQ 121 | | | x | x | x | x | |
| UV LIQ 122 | | | x | x | x | | x |
| UV LIQ 123 | | | | x | x | x | x |

Table 3 abbreviations

| Abbreviation | INCI name | Cas. No. |
|---|---|---|
| DHHB | Diethylamino Hydroxy Benzoyl Hexyl Benzoate | 302776-68-7 |
| EHDP | Ethylhexyl Dimethyl PABA | 21245-02-3 |
| EHMC | Ethylhexyl Methoxycinnamate | 5466-77-3 |
| EHS | Ethylhexyl Salicylate | 118-60-5 |
| HMS | Homosalate | 118-56-9 |
| IMC | Isoamyl p-Methoxycinnamate | 71617-10-2 |
| OCR | Octocrylene | 6197-30-4 |
| PS15 | Polysilicone-15 | 207574-74-1 |

The following mixtures of aqueous soluble or dispersible UV filters (Table 4) can be mixed together with the benzylidene compounds according to the present invention:

TABLE 4

List of aqueous soluble or dispersible UV filters

| Comb. Nr | BP5 | BCSA | CBM | DPDT | MBBT | PABA | p-PABA | PBSA | TDSA | TiO2 | ZnO | TBT | DHHM |
|---|---|---|---|---|---|---|---|---|---|---|---|---|---|
| UV WAT 1 | x | | | | | | | | | | | | |
| UV WAT 2 | | x | | | | | | | | | | | |
| UV WAT 3 | | | x | | | | | | | | | | |
| UV WAT 4 | | | | x | | | | | | | | | |
| UV WAT 5 | | | | | x | | | | | | | | |
| UV WAT 6 | | | | | | x | | | | | | | |
| UV WAT 7 | | | | | | | x | | | | | | |
| UV WAT 8 | | | | | | | | x | | | | | |
| UV WAT 9 | | | | | | | | | x | | | | |
| UV WAT 10 | | | | | | | | | | x | | | |
| UV WAT 11 | | | | | | | | | | | x | | |
| UV WAT 12 | | | | | | | | | | | | x | |
| UV WAT 13 | | | | | | | | | | | | | x |
| UV WAT 14 | x | x | | | | | | | | | | | |
| UV WAT 15 | x | | x | | | | | | | | | | |
| UV WAT 16 | x | | | x | | | | | | | | | |
| UV WAT 17 | x | | | | x | | | | | | | | |
| UV WAT 18 | x | | | | | x | | | | | | | |
| UV WAT 19 | x | | | | | | x | | | | | | |
| UV WAT 20 | x | | | | | | | x | | | | | |
| UV WAT 21 | x | | | | | | | | x | | | | |
| UV WAT 22 | x | | | | | | | | | x | | | |
| UV WAT 23 | x | | | | | | | | | | x | | |
| UV WAT 24 | x | | | | | | | | | | | x | |
| UV WAT 25 | x | | | | | | | | | | | | x |
| UV WAT 26 | | x | x | | | | | | | | | | |
| UV WAT 27 | | x | | x | | | | | | | | | |
| UV WAT 28 | | x | | | x | | | | | | | | |
| UV WAT 29 | | x | | | | x | | | | | | | |
| UV WAT 30 | | x | | | | | x | | | | | | |
| UV WAT 31 | | x | | | | | | x | | | | | |
| UV WAT 32 | | x | | | | | | | x | | | | |
| UV WAT 33 | | x | | | | | | | | x | | | |
| UV WAT 34 | | x | | | | | | | | | x | | |
| UV WAT 35 | | x | | | | | | | | | | x | |
| UV WAT 36 | | x | | | | | | | | | | | x |
| UV WAT 37 | | | x | x | | | | | | | | | |
| UV WAT 38 | | | x | | x | | | | | | | | |

TABLE 4-continued

List of aqueous soluble or dispersible UV filters

| Filter | | | | | | | | | | |
|---|---|---|---|---|---|---|---|---|---|---|
| UV WAT 39 | | x | | x | | | | | | |
| UV WAT 40 | | x | | | x | | | | | |
| UV WAT 41 | | x | | | | x | | | | |
| UV WAT 42 | | x | | | | | x | | | |
| UV WAT 43 | | x | | | | | | x | | |
| UV WAT 44 | | x | | | | | | | x | |
| UV WAT 45 | | x | | | | | | | | x |
| UV WAT 46 | | x | | | | | | | | x |
| UV WAT 47 | | | x | x | | | | | | |
| UV WAT 48 | | | x | | x | | | | | |
| UV WAT 49 | | | x | | | x | | | | |
| UV WAT 50 | | | x | | | | x | | | |
| UV WAT 51 | | | x | | | | | x | | |
| UV WAT 52 | | | x | | | | | | x | |
| UV WAT 53 | | | x | | | | | | | x |
| UV WAT 54 | | | x | | | | | | x | |
| UV WAT 55 | | | x | | | | | | | x |
| UV WAT 56 | | | | x | x | | | | | |
| UV WAT 57 | | | | x | | x | | | | |
| UV WAT 58 | | | | x | | | x | | | |
| UV WAT 59 | | | | x | | | | x | | |
| UV WAT 60 | | | | x | | | | | x | |
| UV WAT 61 | | | | x | | | | | | x |
| UV WAT 62 | | | | x | | | | | x | |
| UV WAT 63 | | | | x | | | | | | x |
| UV WAT 64 | | | | | x | x | | | | |
| UV WAT 65 | | | | | x | | x | | | |
| UV WAT 66 | | | | | x | | | x | | |
| UV WAT 67 | | | | | x | | | | x | |
| UV WAT 68 | | | | | x | | | | | x |
| UV WAT 69 | | | | | x | | | | x | |
| UV WAT 70 | | | | | x | | | | | x |
| UV WAT 71 | | | | | | x | x | | | |
| UV WAT 72 | | | | | | x | | x | | |
| UV WAT 73 | | | | | | x | | | x | |
| UV WAT 74 | | | | | | x | | | | x |
| UV WAT 75 | | | | | | x | | | x | |
| UV WAT 76 | | | | | | x | | | | x |
| UV WAT 77 | | | | | | | x | x | | |
| UV WAT 78 | | | | | | | x | | x | |
| UV WAT 79 | | | | | | | x | | | x |
| UV WAT 80 | | | | | | | x | | x | |
| UV WAT 81 | | | | | | | x | | | x |
| UV WAT 82 | | | | | | | | x | x | |
| UV WAT 83 | | | | | | | | x | | x |
| UV WAT 84 | | | | | | | | x | x | |
| UV WAT 85 | | | | | | | | x | | x |
| UV WAT 86 | | | | | | | | | x | x |
| UV WAT 87 | | | | | | | | | x | x |
| UV WAT 88 | | | | | | | | | x | x |
| UV WAT 89 | | | | | | | | | x | x |
| UV WAT 90 | | | | | | | | | x | x |
| UV WAT 91 | | | | | | | | | x | x |
| UV WAT 92 | x | x | x | | | | | | | |
| UV WAT 93 | x | x | | x | | | | | | |
| UV WAT 94 | x | x | | | x | | | | | |
| UV WAT 95 | x | x | | | | x | | | | |
| UV WAT 96 | x | x | | | | | x | | | |
| UV WAT 97 | x | x | | | | | | x | | |
| UV WAT 98 | x | x | | | | | | | x | |
| UV WAT 99 | x | x | | | | | | | x | |
| UV WAT 100 | x | x | | | | | | | | x |
| UV WAT 101 | x | x | | | | | | | | x |
| UV WAT 102 | x | x | | | | | | | | x |
| UV WAT 103 | x | | x | x | | | | | | |
| UV WAT 104 | x | | x | | x | | | | | |
| UV WAT 105 | x | | x | | | x | | | | |
| UV WAT 106 | x | | x | | | | x | | | |
| UV WAT 107 | x | | x | | | | | x | | |
| UV WAT 108 | x | | x | | | | | | x | |
| UV WAT 109 | x | | x | | | | | | x | |
| UV WAT 110 | x | | x | | | | | | | x |
| UV WAT 111 | x | | x | | | | | | | x |
| UV WAT 112 | x | | x | | | | | | | x |
| UV WAT 113 | x | | | x | x | | | | | |
| UV WAT 114 | x | | | x | | x | | | | |
| UV WAT 115 | x | | | x | | | x | | | |
| UV WAT 116 | x | | | x | | | | x | | |

TABLE 4-continued

List of aqueous soluble or dispersible UV filters

| | C1 | C2 | C3 | C4 | C5 | C6 | C7 | C8 | C9 |
|---|---|---|---|---|---|---|---|---|---|
| UV WAT 117 | x | | x | | | x | x | | |
| UV WAT 118 | x | | x | | | | x | | |
| UV WAT 119 | x | | x | | | | | x | |
| UV WAT 120 | x | | x | | | | | x | |
| UV WAT 121 | x | | x | | | | | | x |
| UV WAT 122 | x | | | x | x | | | | |
| UV WAT 123 | x | | | x | | x | | | |
| UV WAT 124 | x | | | x | | x | | | |
| UV WAT 125 | x | | | x | | | x | | |
| UV WAT 126 | x | | | x | | | x | | |
| UV WAT 127 | x | | | x | | | | x | |
| UV WAT 128 | x | | | x | | | | x | |
| UV WAT 129 | x | | | x | | | | | x |
| UV WAT 130 | x | | | | x | x | | | |
| UV WAT 131 | x | | | | x | | x | | |
| UV WAT 132 | x | | | | x | | x | | |
| UV WAT 133 | x | | | | x | | x | | |
| UV WAT 134 | x | | | | x | | | x | |
| UV WAT 135 | x | | | | x | | | x | |
| UV WAT 136 | x | | | | x | | | | x |
| UV WAT 137 | x | | | | | x | x | | |
| UV WAT 138 | x | | | | | x | x | | |
| UV WAT 139 | x | | | | | x | | x | |
| UV WAT 140 | x | | | | | x | | x | |
| UV WAT 141 | x | | | | | x | | x | |
| UV WAT 142 | x | | | | | x | | | x |
| UV WAT 143 | x | | | | | | x | x | |
| UV WAT 144 | x | | | | | | x | x | |
| UV WAT 145 | x | | | | | | x | | x |
| UV WAT 146 | x | | | | | | x | | x |
| UV WAT 147 | x | | | | | | x | | x |
| UV WAT 148 | x | | | | | | | x | x |
| UV WAT 149 | x | | | | | | | x | x |
| UV WAT 150 | x | | | | | | | x | x |
| UV WAT 151 | x | | | | | | | x | x |
| UV WAT 152 | x | | | | | | | | x |
| UV WAT 153 | x | | | | | | | | x |
| UV WAT 154 | x | | | | | | | | x |
| UV WAT 155 | x | | | | | | | | x |
| UV WAT 156 | x | | | | | | | | x |
| UV WAT 157 | x | | | | | | | | x |
| UV WAT 158 | | x | x | x | | | | | |
| UV WAT 159 | | x | x | | x | | | | |
| UV WAT 160 | | x | x | | x | | | | |
| UV WAT 161 | | x | x | | | x | | | |
| UV WAT 162 | | x | x | | | x | | | |
| UV WAT 163 | | x | x | | | x | | | |
| UV WAT 164 | | x | x | | | | x | | |
| UV WAT 165 | | x | x | | | | x | | |
| UV WAT 166 | | x | x | | | | | x | |
| UV WAT 167 | | x | x | | | | | | x |
| UV WAT 168 | | x | | x | x | | | | |
| UV WAT 169 | | x | | x | x | | | | |
| UV WAT 170 | | x | | x | | x | | | |
| UV WAT 171 | | x | | x | | x | | | |
| UV WAT 172 | | x | | x | | x | | | |
| UV WAT 173 | | x | | x | | | x | | |
| UV WAT 174 | | x | | x | | | x | | |
| UV WAT 175 | | x | | x | | | | x | |
| UV WAT 176 | | x | | x | | | | | x |
| UV WAT 177 | | x | | | x | x | | | |
| UV WAT 178 | | x | | | x | x | | | |
| UV WAT 179 | | x | | | x | | x | | |
| UV WAT 180 | | x | | | x | | x | | |
| UV WAT 181 | | x | | | x | | | x | |
| UV WAT 182 | | x | | | x | | | x | |
| UV WAT 183 | | x | | | x | | | | x |
| UV WAT 184 | | x | | | x | | | | x |
| UV WAT 185 | | x | | | | x | x | | |
| UV WAT 186 | | x | | | | x | x | | |
| UV WAT 187 | | x | | | | x | | x | |
| UV WAT 188 | | x | | | | x | | x | |
| UV WAT 189 | | x | | | | x | | | x |
| UV WAT 190 | | x | | | | x | | | x |
| UV WAT 191 | | x | | | | x | | | x |
| UV WAT 192 | | x | | | | | x | x | |
| UV WAT 193 | | x | | | | | x | x | |
| UV WAT 194 | | x | | | | | x | x | |

TABLE 4-continued

List of aqueous soluble or dispersible UV filters

| Name | C1 | C2 | C3 | C4 | C5 | C6 | C7 | C8 |
|---|---|---|---|---|---|---|---|---|
| UV WAT 195 | x |   |   | x |   | x |   |   |
| UV WAT 196 | x |   |   | x |   |   | x |   |
| UV WAT 197 | x |   |   | x |   |   |   | x |
| UV WAT 198 | x |   |   |   | x | x |   |   |
| UV WAT 199 | x |   |   |   | x |   | x |   |
| UV WAT 200 | x |   |   |   | x |   | x |   |
| UV WAT 201 | x |   |   |   | x |   |   | x |
| UV WAT 202 | x |   |   |   | x |   |   | x |
| UV WAT 203 | x |   |   |   |   | x | x |   |
| UV WAT 204 | x |   |   |   |   | x | x |   |
| UV WAT 205 | x |   |   |   |   | x |   | x |
| UV WAT 206 | x |   |   |   |   | x |   | x |
| UV WAT 207 | x |   |   |   |   |   | x | x |
| UV WAT 208 | x |   |   |   |   |   | x | x |
| UV WAT 209 | x |   |   |   |   |   | x | x |
| UV WAT 210 | x |   |   |   |   |   | x | x |
| UV WAT 211 | x |   |   |   |   |   | x | x |
| UV WAT 212 | x |   |   |   |   |   | x | x |
| UV WAT 213 |   | x | x | x |   |   |   |   |
| UV WAT 214 |   | x | x |   | x |   |   |   |
| UV WAT 215 |   | x | x |   | x |   |   |   |
| UV WAT 216 |   | x | x |   | x |   |   |   |
| UV WAT 217 |   | x | x |   |   | x |   |   |
| UV WAT 218 |   | x | x |   |   | x |   |   |
| UV WAT 219 |   | x | x |   |   |   | x |   |
| UV WAT 220 |   | x | x |   |   |   | x |   |
| UV WAT 221 |   | x | x |   |   |   |   | x |
| UV WAT 222 |   | x |   | x | x |   |   |   |
| UV WAT 223 |   | x |   | x | x |   |   |   |
| UV WAT 224 |   | x |   | x |   | x |   |   |
| UV WAT 225 |   | x |   | x |   | x |   |   |
| UV WAT 226 |   | x |   | x |   |   | x |   |
| UV WAT 227 |   | x |   | x |   |   | x |   |
| UV WAT 228 |   | x |   | x |   |   | x |   |
| UV WAT 229 |   | x |   | x |   |   |   | x |
| UV WAT 230 |   | x |   |   | x | x |   |   |
| UV WAT 231 |   | x |   |   | x | x |   |   |
| UV WAT 232 |   | x |   |   | x |   | x |   |
| UV WAT 233 |   | x |   |   | x |   | x |   |
| UV WAT 234 |   | x |   |   | x |   | x |   |
| UV WAT 235 |   | x |   |   | x |   | x |   |
| UV WAT 236 |   | x |   |   | x |   |   | x |
| UV WAT 237 |   | x |   |   |   | x | x |   |
| UV WAT 238 |   | x |   |   |   | x | x |   |
| UV WAT 239 |   | x |   |   |   | x |   | x |
| UV WAT 240 |   | x |   |   |   | x |   | x |
| UV WAT 241 |   | x |   |   |   | x |   | x |
| UV WAT 242 |   | x |   |   |   | x |   | x |
| UV WAT 243 |   | x |   |   |   |   | x | x |
| UV WAT 244 |   | x |   |   |   |   | x | x |
| UV WAT 245 |   | x |   |   |   |   | x | x |
| UV WAT 246 |   | x |   |   |   |   | x | x |
| UV WAT 247 |   | x |   |   |   |   |   | x |
| UV WAT 248 |   | x |   |   |   |   | x | x |
| UV WAT 249 |   | x |   |   |   |   | x | x |
| UV WAT 250 |   | x |   |   |   |   | x | x |
| UV WAT 251 |   | x |   |   |   |   |   | x |
| UV WAT 252 |   | x |   |   |   |   | x | x |
| UV WAT 253 |   | x |   |   |   |   | x | x |
| UV WAT 254 |   | x |   |   |   |   | x | x |
| UV WAT 255 |   | x |   |   |   |   | x | x |
| UV WAT 256 |   | x |   |   |   |   | x | x |
| UV WAT 257 |   | x |   |   |   |   | x | x |
| UV WAT 258 |   |   | x | x | x |   |   |   |
| UV WAT 259 |   |   | x | x |   | x |   |   |
| UV WAT 260 |   |   | x | x |   | x |   |   |
| UV WAT 261 |   |   | x | x |   |   | x |   |
| UV WAT 262 |   |   | x | x |   |   | x |   |
| UV WAT 263 |   |   | x | x |   |   | x |   |
| UV WAT 264 |   |   | x | x |   |   | x |   |
| UV WAT 265 |   |   | x | x |   |   |   | x |
| UV WAT 266 |   |   | x |   | x | x |   |   |
| UV WAT 267 |   |   | x |   | x | x |   |   |
| UV WAT 268 |   |   | x |   | x |   | x |   |
| UV WAT 269 |   |   | x |   | x |   | x |   |
| UV WAT 270 |   |   | x |   | x |   | x |   |
| UV WAT 271 |   |   | x |   |   | x |   |   |
| UV WAT 272 |   |   | x |   |   | x |   | x |

TABLE 4-continued

List of aqueous soluble or dispersible UV filters

| | | | | | | | | |
|---|---|---|---|---|---|---|---|---|
| UV WAT 273 | x | | x | x | | | | |
| UV WAT 274 | x | | x | | x | | | |
| UV WAT 275 | x | | x | | | x | | |
| UV WAT 276 | x | | x | | | | x | |
| UV WAT 277 | x | | x | | | | x | |
| UV WAT 278 | x | | x | | | | | x |
| UV WAT 279 | x | | | x | x | | | |
| UV WAT 280 | x | | | x | | x | | |
| UV WAT 281 | x | | | x | | | x | |
| UV WAT 282 | x | | | x | | | x | |
| UV WAT 283 | x | | | x | | | | x |
| UV WAT 284 | x | | | | x | x | | |
| UV WAT 285 | x | | | | x | | x | |
| UV WAT 286 | x | | | | x | | x | |
| UV WAT 287 | x | | | | x | | | x |
| UV WAT 288 | x | | | | | x | x | |
| UV WAT 289 | x | | | | | x | x | |
| UV WAT 290 | x | | | | | x | | x |
| UV WAT 291 | x | | | | | | x | x |
| UV WAT 292 | x | | | | | | x | x |
| UV WAT 293 | x | | | | | | x | x |
| UV WAT 294 | | x | x | x | | | | |
| UV WAT 295 | | x | x | | x | | | |
| UV WAT 296 | | x | x | | | x | | |
| UV WAT 297 | | x | x | | | | x | |
| UV WAT 298 | | x | x | | | | x | |
| UV WAT 299 | | x | x | | | | x | |
| UV WAT 300 | | x | x | | | | | x |
| UV WAT 301 | | x | | x | x | | | |
| UV WAT 302 | | x | | x | | x | | |
| UV WAT 303 | | x | | x | | | x | |
| UV WAT 304 | | x | | x | | | x | |
| UV WAT 305 | | x | | x | | | x | |
| UV WAT 306 | | x | | x | | | | x |
| UV WAT 307 | | x | | | x | x | | |
| UV WAT 308 | | x | | | x | | x | |
| UV WAT 309 | | x | | | x | | x | |
| UV WAT 310 | | x | | | x | | x | |
| UV WAT 311 | | x | | | x | | | x |
| UV WAT 312 | | x | | | | x | x | |
| UV WAT 313 | | x | | | | x | x | |
| UV WAT 314 | | x | | | | x | | x |
| UV WAT 315 | | x | | | | x | | x |
| UV WAT 316 | | x | | | | | x | x |
| UV WAT 317 | | x | | | | | x | x |
| UV WAT 318 | | x | | | | | x | x |
| UV WAT 319 | | x | | | | | x | x |
| UV WAT 320 | | x | | | | | x | x |
| UV WAT 321 | | x | | | | | x | x |
| UV WAT 322 | | | x | x | x | | | |
| UV WAT 323 | | | x | x | | x | | |
| UV WAT 324 | | | x | x | | | x | |
| UV WAT 325 | | | x | x | | | x | |
| UV WAT 326 | | | x | x | | | x | |
| UV WAT 327 | | | x | x | | | | x |
| UV WAT 328 | | | x | | x | x | | |
| UV WAT 329 | | | x | | x | | x | |
| UV WAT 330 | | | x | | x | | x | |
| UV WAT 331 | | | x | | x | | x | |
| UV WAT 332 | | | x | | x | | | x |
| UV WAT 333 | | | x | | | x | x | |
| UV WAT 334 | | | x | | | x | x | |
| UV WAT 335 | | | x | | | x | x | |
| UV WAT 336 | | | x | | | x | | x |
| UV WAT 337 | | | x | | | | x | x |
| UV WAT 338 | | | x | | | | x | x |
| UV WAT 339 | | | x | | | | x | x |
| UV WAT 340 | | | x | | | | x | x |
| UV WAT 341 | | | x | | | | x | x |
| UV WAT 342 | | | x | | | | x | x |
| UV WAT 343 | | | | x | x | x | | |
| UV WAT 344 | | | | x | x | | x | |
| UV WAT 345 | | | | x | x | | x | |
| UV WAT 346 | | | | x | x | | x | |
| UV WAT 347 | | | | x | x | | | x |
| UV WAT 348 | | | | x | | x | x | |
| UV WAT 349 | | | | x | | x | x | |
| UV WAT 350 | | | | x | | x | x | |

TABLE 4-continued

List of aqueous soluble or dispersible UV filters

| | C1 | C2 | C3 | C4 | C5 | C6 |
|---|---|---|---|---|---|---|
| UV WAT 351 | x | | x | x | | x |
| UV WAT 352 | x | | | x | x | |
| UV WAT 353 | x | | | x | | x |
| UV WAT 354 | x | | | x | | x |
| UV WAT 355 | x | | | | x | x |
| UV WAT 356 | x | | | | x | x |
| UV WAT 357 | x | | | | x | x |
| UV WAT 358 | | x | x | x | | |
| UV WAT 359 | | x | x | | x | |
| UV WAT 360 | | x | x | | x | |
| UV WAT 361 | | x | x | | | x |
| UV WAT 362 | | x | | x | x | |
| UV WAT 363 | | x | | x | | x |
| UV WAT 364 | | x | x | | | x |
| UV WAT 365 | | x | | | x | x |
| UV WAT 366 | | x | | | x | x |
| UV WAT 367 | | x | | | x | x |
| UV WAT 368 | | | x | x | x | |
| UV WAT 369 | | | x | x | | x |
| UV WAT 370 | | | x | x | | x |
| UV WAT 371 | | | x | | x | x |
| UV WAT 372 | | | x | | x | x |
| UV WAT 373 | | | x | | x | x |
| UV WAT 374 | | | | x | x | x |
| UV WAT 375 | | | | x | x | x |
| UV WAT 376 | | | | x | | x x |
| UV WAT 377 | | | | | x | x x |

Table 4 Abbreviations

| Abbreviations | INCI name | Particle size range | Cas. No. |
|---|---|---|---|
| BP5 | Benzophenone-5 | | 6628-37-1 |
| BCSA | Benzydilene Camphor Sulfonic Acid | | 56039-58-8 |
| CBM | Camphor Benzalkonium Methosulfate | | 52793-97-2 |
| DPDT | Disodium Phenyl Dibenzylmidazole Tetrasulfonate | | 180898-37-7 |
| MBBT | Micronized Methylene Bis-Benzotriazolyl Tatramethylbutylphenol | 50-200 nm | 103597-45-1 |
| PABA | PABA | | 150-13-0 |
| p-PABA | PEG-25 PABA | | 113010-52-9 |
| PBSA | Phenylbenzimidazole Sulfonic Acid | | 27503-81-7 |
| TDSA | Terephthalylidene Dicamphor Sulfonic Acid | | 90457-82-2 |
| TiO$_2$ | Titanium Dioxide | 10-50 nm | 13463-67-7 |
| ZnO | Zinc Oxide | 20-100 nm | 131413-2 |
| TB | Micronized Tris-Biphenyl Triazine | 50-200 nm | 31274-51-8 |
| DHHM | Micronized (2-{4-[2-(4-Diethylamino-2-hydroxy-benzoyl)-benzoyl]-piperazine-1-carbonyl}-phenyl)-(4-diethylamino-2-hydroxy-phenyl)-methanone | 50-200 nm | |

UV FILTER COMBINATION EXAMPLES

In all of the UV filter combinations listed before in the Table "X" represents a specific UV filter. The weight ratio of each specific UV absorber (based on the weight of all UV absorbers in the combination) can for example range from 0.01 to 0.99, especially 0.1 to 0.9, preferably 0.2 to 0.8. (for example 0.3).

Further UV Filter Combination Examples are the Following:

In all of the UV filter combinations listed before the weight ratio of the UV absorbers (based on the weight of all UV absorbers in the combination) is:

(a) for Combinations of Two UV Absorbers:
1:1 or 1:2 or 2:1 or 1:3 or 3:1.

(b) for Combinations of Three UV Absorbers:
1:1:1 or 1:2:1 or 1:1:2 or 2:1:1 or 1:2:2 or 2:1:2 or 2:2:1 or 1:3:1 or 1:1:3 or 3:1:1 or 1:3:3 or 3:1:3 or 3:3:1 or 1:2:3 or 1:3:2 or 2:1:3 or 2:3:1 or 3:1:2 or 3:2:1.

(c) for Combinations of Four UV Absorbers:
1:1:1:1 or 1:1:2:1 or 1:1:1:2 or 1:2:1:1 or 2:1:1:1 or 1:1:1:3 or 1:1:3:1
or 1:3:1:1 or 3:1:1:1 or 1:2:2:1 or 2:1:2:1 or 2:2:1:1 or 2:1:1:2 or
1:3:31 or 3:1:3:1 or 3:3:1:1 or 3:1:1:3 or 1:2:3:1 or 1:3:2:1 or 1:1:2:3
or 1:1:3:2 or 2:1:1:3 or 2:1:3:1 or 2:3:1:1 or 3:1:1.2 or 3:2:1:1
or 3:1:2:1.

Formulation Examples

In the following formulation examples:

The new UV filter may be (as described in Table 1) P-01 or P-02 or P-03 or P-04 or P-05 or P-06 or P-07 or P-08 or P-09 or P-10 or P-11 or P-12 or P-13 or P-14 or P-15 or P-16.

"UV SOL" may be (as described in Table 2) UV SOL 1, or UV SOL 2, or UV SOL 3, or UV SOL 4, or UV SOL 5, or UV SOL 6, or UV SOL 7, or UV SOL 8, or UV SOL 9, or UV SOL 10, or UV SOL 11, or UV SOL 12, or UV SOL 13, or UV SOL 14, or UV SOL 15, or UV SOL 16, or UV SOL 17, or UV SOL 18, or UV SOL 19, or UV SOL 20, or UV SOL 21, or UV SOL 22, or UV SOL 23, or UV SOL 24, or UV SOL 25, or UV SOL 26, or UV SOL 27, or UV SOL 28, or UV SOL 29, or UV SOL 30, or UV SOL 31, or UV SOL 32, or UV SOL 33, or UV SOL 34, or UV SOL 35, or UV SOL 36, or UV SOL 37, or UV SOL 38, or UV SOL 39, or UV SOL 40, or UV SOL 41, or UV SOL 42, or UV SOL 43, or UV SOL 44, or UV SOL 45, or UV SOL 46, or UV SOL 47, or UV SOL 48, or UV SOL 49, or UV SOL 50, or UV SOL 51, or UV SOL 52, or UV SOL 53, or UV SOL 54, or UV SOL 55, or UV SOL 56, or UV SOL 57, or UV SOL 58, or UV SOL 59, or UV SOL 60, or UV SOL 61, or UV SOL 62, or UV SOL 63, or UV SOL 64, or UV SOL 65, or UV SOL 66, or UV SOL 67, or UV SOL 68, or UV SOL 69, or UV SOL 70, or UV SOL 71, or UV SOL 72, or UV SOL 73, or UV SOL 74, or UV SOL 75, or UV SOL 76, or UV SOL 77, or UV SOL 78, or UV SOL 79, or UV SOL 80, or UV SOL 81, or UV SOL 82, or UV SOL 83, or UV SOL 84, or UV SOL 85, or UV SOL 86, or UV SOL 87, or UV SOL 88, or UV SOL 89, or UV SOL 90, or UV SOL 91, or UV SOL 92, or UV SOL 93, or UV SOL 94, or UV SOL 95, or UV SOL 96, or UV SOL 97, or UV SOL 98, or UV SOL 99, or UV SOL 100, or UV SOL 101, or UV SOL 102, or UV SOL 103, or UV SOL 104, or UV SOL 105, or UV SOL 106, or UV SOL 107, or UV SOL 108, or UV SOL 109, or UV SOL 110, or UV SOL 111, or UV SOL 112, or UV SOL 113, or UV SOL 114, or UV SOL 115, or UV SOL 116, or UV SOL 117, or UV SOL 118, or UV SOL 119, or UV SOL 120, or UV SOL 121, or UV SOL 122, or UV SOL 123, or UV SOL 124, or UV SOL 125, or UV SOL 126, or UV SOL 127, or UV SOL 128, or UV SOL 129, or UV SOL 130, or UV SOL 131, or UV SOL 132, or UV SOL 133, or UV SOL 134, or UV SOL 135, or UV SOL 136, or UV SOL 137, or UV SOL 138, or UV SOL 139, or UV SOL 140, or UV SOL 141, or UV SOL 142, or UV SOL 143, or UV SOL 144, or UV SOL 145, or UV SOL 146, or UV SOL 147, or UV SOL 148, or UV SOL 149, or UV SOL 150, or UV SOL 151, or UV SOL 152, or UV SOL 153, or UV SOL 154, or UV SOL 155, or UV SOL 156, or UV SOL 157, or UV SOL 158, or UV SOL 159, or UV SOL 160, or UV SOL 161, or UV SOL 162, or UV SOL 163, or UV SOL 164, or UV SOL 165, or UV SOL 166, or UV SOL 167, or UV SOL 168, or UV SOL 169, or UV SOL 170, or UV SOL 171, or UV SOL 172, or UV SOL 173, or UV SOL 174, or UV SOL 175, or UV SOL 176, or UV SOL 177, or UV SOL 178, or UV SOL 179, or UV SOL 180, or UV SOL 181, or UV SOL 182, or UV SOL 183, or UV SOL 184, or UV SOL 185, or UV SOL 186, or UV SOL 187, or UV SOL 188, or UV SOL 189, or UV SOL 190, or UV SOL 191, or UV SOL 192, or UV SOL 193, or UV SOL 194, or UV SOL 195, or UV SOL 196, or UV SOL 197, or UV SOL 198, or UV SOL 199, or UV SOL 200, or UV SOL 201, or UV SOL 202, or UV SOL 203, or UV SOL 204, or UV SOL 205, or UV SOL 206, or UV SOL 207, or UV SOL 208, or UV SOL 209, or UV SOL 210, or UV SOL 211, or UV SOL 212, or UV SOL 213, or UV SOL 214, or UV SOL 215, or UV SOL 216, or UV SOL 217, or UV SOL 218, or UV SOL 219, or UV SOL 220, or UV SOL 221, or UV SOL 222, or UV SOL 223, or UV SOL 224, or UV SOL 225, or UV SOL 226, or UV SOL 227, or UV SOL 228, or UV SOL 229, or UV SOL 230, or UV SOL 231, or UV SOL 232, or UV SOL 233, or UV SOL 234, or UV SOL 235, or UV SOL 236, or UV SOL 237, or UV SOL 238, or UV SOL 239, or UV SOL 240, or UV SOL 241, or UV SOL 242, or UV SOL 243, or UV SOL 244, or UV SOL 245, or UV SOL 246, or UV SOL 247, or UV SOL 248, or UV SOL 249, or UV SOL 250, or UV SOL 251, or UV SOL 252, or UV SOL 253;

"UV LIQ" may be (as described in Table 3) UV LIQ 1, or UV LIQ 2, or UV LIQ 3, or UV LIQ 4, or UV LIQ 5, or UV LIQ 6, or UV LIQ 7, or UV LIQ 8, or UV LIQ 9, or UV LIQ 10, or UV LIQ 11, or UV LIQ 12, or UV LIQ 13, or UV LIQ 14, or UV LIQ 15, or UV LIQ 16, or UV LIQ 17, or UV LIQ 18, or UV LIQ 19, or UV LIQ 20, or UV LIQ 21, or UV LIQ 22, or UV LIQ 23, or UV LIQ 24, or UV LIQ 25, or UV LIQ 26, or UV LIQ 27, or UV LIQ 28, or UV LIQ 29, or UV LIQ 30, or UV LIQ 31, or UV LIQ 32, or UV LIQ 33, or UV LIQ 34, or UV LIQ 35, or UV LIQ 36, or UV LIQ 37, or UV LIQ 38, or UV LIQ 39, or UV LIQ 40, or UV LIQ 41, or UV LIQ 42, or UV LIQ 43, or UV LIQ 44, or UV LIQ 45, or UV LIQ 46, or UV LIQ 47, or UV LIQ 48, or UV LIQ 49, or UV LIQ 50, or UV LIQ 51, or UV LIQ 52, or UV LIQ 53, or UV LIQ 54, or UV LIQ 55, or UV LIQ 56, or UV LIQ 57, or UV LIQ 58, or UV LIQ 59, or UV LIQ 60, or UV LIQ 61, or UV LIQ 62, or UV LIQ 63, or UV LIQ 64, or UV LIQ 65, or UV LIQ 66, or UV LIQ 67, or UV LIQ 68, or UV LIQ 69, or UV LIQ 70, or UV LIQ 71, or UV LIQ 72, or UV LIQ 73, or UV LIQ 74, or UV LIQ 75, or UV LIQ 76, or UV LIQ 77, or UV LIQ 78, or UV LIQ 79, or UV LIQ 80, or UV LIQ 81, or UV LIQ 82, or UV LIQ 83, or UV LIQ 84, or UV LIQ 85, or UV LIQ 86, or UV LIQ 87, or UV LIQ 88, or UV LIQ 89, or UV LIQ 90, or UV LIQ 91, or UV LIQ 92, or UV LIQ 93, or UV LIQ 94, or UV LIQ 95, or UV LIQ 96, or UV LIQ 97, or UV LIQ 98, or UV LIQ 99, or UV LIQ 100, or UV LIQ 101, or UV LIQ 102, or UV LIQ 103, or UV LIQ 104, or UV LIQ 105, or UV LIQ 106, or UV LIQ 107, or UV LIQ 108, or UV LIQ 109, or UV LIQ 110, or UV LIQ 111, or UV LIQ 112, or UV LIQ 113, or UV LIQ 114, or UV LIQ 115, or UV LIQ 116, or UV LIQ 117, or UV LIQ 118, or UV LIQ 119, or UV LIQ 120, or UV LIQ 121, or UV LIQ 122, or UV LIQ 123;

"UV WAT" may be (as described in Table 4) UV WAT 1, or UV WAT 2, or UV WAT 3, or UV WAT 4, or UV WAT 5, or UV WAT 6, or UV WAT 7, or UV WAT 8, or UV WAT 9, or UV WAT 10, or UV WAT 11, or UV WAT 12, or UV WAT 13, or UV WAT 14, or UV WAT 15, or UV WAT 16, or UV WAT 17, or UV WAT 18, or UV WAT 19, or UV WAT 20, or UV WAT 21, or UV WAT 22, or UV WAT 23, or UV WAT 24, or UV WAT 25, or UV WAT 26, or UV WAT 27, or UV WAT 28, or UV WAT 29, or UV WAT 30, or UV WAT 31, or UV WAT 32, or UV WAT 33, or UV WAT 34, or UV WAT 35, or UV WAT 36, or UV WAT 37, or UV WAT 38, or UV WAT 39, or UV WAT 40, or UV WAT 41, or UV WAT 42, or UV WAT 43, or UV WAT 44, or UV WAT 45, or UV WAT 46, or UV WAT 47, or UV WAT 48, or UV WAT 49, or UV WAT 50, or UV WAT 51, or UV WAT 52, or UV WAT 53, or UV WAT 54, or UV WAT 55, or UV WAT 56, or UV WAT 57, or UV WAT 58, or UV WAT 59, or UV WAT 60, or UV WAT 61, or UV WAT 62, or UV WAT 63, or UV WAT 64, or UV WAT 65, or UV WAT 66, or UV WAT 67, or UV WAT 68, or UV WAT 69, or UV WAT 70, or UV WAT 71, or UV WAT 72, or UV WAT 73, or UV WAT 74, or UV WAT 75, or UV WAT 76, or UV WAT 77, or UV WAT 78, or UV WAT 79, or UV WAT 80, or UV WAT 81, or UV WAT 82, or UV WAT 83, or UV WAT 84, or UV WAT 85, or UV WAT 86, or UV WAT 87, or UV WAT 88, or UV WAT 89, or UV WAT 90, or UV WAT 91, or UV WAT 92, or UV WAT 93, or UV WAT 94, or UV WAT 95, or UV WAT 96, or UV WAT 97, or UV WAT 98, or UV WAT 99, or UV WAT 100, or UV WAT 101, or UV WAT 102, or UV WAT 103, or UV WAT 104, or UV WAT 105, or UV WAT 106, or UV WAT 107, or UV WAT 108, or UV WAT 109, or UV WAT 110, or UV WAT 111, or UV WAT 112, or UV WAT 113, or UV WAT 114, or UV WAT 115, or UV WAT 116, or UV WAT 117, or UV WAT 118, or UV WAT 119, or UV WAT 120, or UV WAT 121, or UV WAT 122, or UV WAT 123, or UV WAT 124, or UV WAT 125, or UV WAT 126, or UV WAT 127, or UV WAT 128, or UV WAT 129, or UV WAT 130, or UV WAT 131, or UV WAT 132, or UV WAT 133, or UV WAT 134, or UV WAT 135, or UV WAT 136, or UV WAT 137, or UV WAT 138, or UV WAT 139, or UV WAT 140, or UV WAT 141, or UV WAT 142, or UV WAT 143, or UV WAT 144, or UV WAT 145, or UV WAT 146, or UV WAT 147, or UV WAT 148, or UV WAT 149, or UV WAT 150, or UV WAT 151, or UV WAT 152, or UV WAT 153, or UV WAT 154, or UV WAT 155, or UV WAT 156, or UV WAT 157, or UV WAT 158, or UV WAT 159, or UV WAT 160, or UV WAT 161, or UV WAT 162, or UV WAT 163, or UV WAT 164, or UV WAT 165, or UV WAT 166, or UV WAT 167, or UV WAT 168, or UV WAT 169, or UV WAT 170, or UV WAT 171, or UV WAT 172, or UV WAT 173, or UV WAT 174, or UV WAT 175, or UV WAT 176, or UV WAT 177, or UV WAT 178, or UV WAT 179, or UV WAT 180, or UV WAT 181, or UV WAT 182, or UV WAT 183, or UV WAT 184, or UV WAT 185, or UV WAT 186, or UV WAT 187, or UV WAT 188, or UV WAT 189, or UV WAT 190, or UV WAT 191, or UV WAT 192, or UV WAT 193, or UV WAT 194, or UV WAT 195, or UV WAT 196, or UV WAT 197, or UV WAT 198, or UV WAT 199, or UV WAT 200, or UV WAT 201, or UV WAT 202, or UV WAT 203, or UV WAT 204, or UV WAT 205, or UV WAT 206, or UV WAT 207, or UV WAT 208, or UV WAT 209, or UV WAT 210, or UV WAT 211, or UV WAT 212, or UV WAT 213, or UV WAT 214, or UV WAT 215, or UV WAT 216, or UV WAT 217, or UV WAT 218, or UV WAT 219, or UV WAT 220, or UV WAT 221, or UV WAT 222, or UV WAT 223, or UV WAT 224, or UV WAT 225, or UV WAT 226, or UV WAT 227, or UV WAT 228, or UV WAT 229, or UV WAT 230, or UV WAT 231, or UV WAT 232, or UV WAT 233, or UV WAT 234, or UV WAT 235, or UV WAT 236, or UV WAT 237, or UV WAT 238, or UV WAT 239, or UV WAT 240, or UV WAT 241, or UV WAT 242, or UV WAT 243, or UV WAT 244, or UV WAT 245, or UV WAT 246, or UV WAT 247, or UV WAT 248, or UV WAT 249, or UV WAT 250, or UV WAT 251, or UV WAT 252, or UV WAT 253, or UV WAT 254, or UV WAT 255, or UV WAT 256, or UV WAT 257, or UV WAT 258, or UV WAT 259, or UV WAT 260, or UV WAT 261, or UV WAT 262, or UV WAT 263, or UV WAT 264, or UV WAT 265, or UV WAT 266, or UV WAT 267, or UV WAT 268, or UV WAT 269, or UV WAT 270, or UV WAT 271, or UV WAT 272, or UV WAT 273, or UV WAT 274, or UV WAT 275, or UV WAT 276, or UV WAT 277, or UV WAT 278, or UV WAT 279, or UV WAT 280, or UV WAT 281, or UV WAT 282, or UV WAT 283, or UV WAT 284, or UV WAT 285, or UV WAT 286, or UV WAT 287, or UV WAT 288, or UV WAT 289, or UV WAT 290, or UV WAT 291, or UV WAT 292, or UV WAT 293, or UV WAT 294, or UV WAT 295, or UV WAT 296, or UV WAT 297, or UV WAT 298, or UV WAT 299, or UV WAT 300, or UV WAT 301, or UV WAT 302, or UV WAT 303, or UV WAT 304, or UV WAT 305, or UV WAT 306, or UV WAT 307, or UV WAT 308, or UV WAT 309, or UV WAT 310, or UV WAT 311, or UV WAT 312, or UV WAT 313, or UV WAT 314, or UV WAT 315, or UV WAT 316, or UV WAT 317, or UV WAT 318, or UV WAT 319, or UV WAT 320, or UV WAT 321, or UV WAT 322, or UV WAT 323, or UV WAT 324, or UV WAT 325, or UV WAT 326, or UV WAT 327, or UV WAT 328, or UV WAT 329, or UV WAT 330, or UV WAT 331, or UV WAT 332, or UV WAT 333, or UV WAT 334, or UV WAT 335, or UV WAT 336, or UV WAT 337, or UV WAT 338, or UV WAT 339, or UV WAT 340, or UV WAT 341, or UV WAT 342, or UV WAT 343, or UV WAT 344, or UV WAT 345, or UV WAT 346, or UV WAT 347, or UV WAT 348, or UV WAT 349, or UV WAT 350, or UV WAT 351, or UV WAT 352, or UV WAT 353, or UV WAT 354, or UV WAT 355, or UV WAT 356, or UV WAT 357, or UV WAT 358, or UV WAT 359, or UV WAT 360, or UV WAT 361, or UV WAT 362, or UV WAT 363, or UV WAT 364, or UV WAT 365, or UV WAT 366, or UV WAT 367, or UV WAT 368, or UV WAT 369, or UV WAT 370, or UV WAT 371, or UV WAT 372, or UV WAT 373, or UV WAT 374, or UV WAT 375, or UV WAT 376, or UV WAT 377.

Formulation Examples

| | | Emulsion high Protection | | | | | | | | |
|---|---|---|---|---|---|---|---|---|---|---|
| | | A | B | C | D | E | F | G | H | I |
| | INCI-Name | % w/w | % w/w | % w/w | % w/w | % w/w | % w/w | % w/w | % w/w | % w/w |
| Part A | Cyclomethicone | 7.0 | 7.0 | 7.0 | 7.0 | 7.0 | 7.0 | 7.0 | 7.0 | 7.0 |
| | Ethylhexyl Palmitate | 5.0 | 0.0 | 0.0 | 0.0 | 0.0 | 0.0 | 0.0 | 0.0 | 0.0 |
| | New UV filter | | 3.0 | 15.0 | 5.0 | 10.0 | 5.0 | 8.0 | 5.0 | 15.0 |
| | Glyceryl Stearate | 1.50 | 1.50 | 1.50 | 1.50 | 1.50 | 1.50 | 1.50 | 1.50 | 1.50 |
| | Potassium Cetyl Phosphate | 1.80 | 1.80 | 1.80 | 1.80 | 1.80 | 1.80 | 1.80 | 1.80 | 1.80 |
| | VP/Eicosene Copolymer | 0.60 | 0.60 | 0.60 | 0.60 | 0.60 | 0.60 | 0.60 | 0.60 | 0.60 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| Part B | Aqua | Qs to 100 | Qs to 100 | Qs to 100 | Qs to 100 | Qs to 100 | Qs to 100 | Qs to 100 | Qs to 100 | Qs to 100 |
| | Acrylates/Palmeth-25 Acrylate Copolymer | 0.25 | 0.25 | 0.25 | 0.25 | 0.25 | 0.25 | 0.25 | 0.25 | 0.25 |
| | Glycerin | 6.0 | 6.0 | 6.0 | 6.0 | 6.0 | 6.0 | 6.0 | 6.0 | 6.0 |
| | Disodium EDTA | 0.20 | 0.20 | 0.20 | 0.20 | 0.20 | 0.20 | 0.20 | 0.20 | 0.20 |
| | UV WAT | | 5.0 | 5.0 | 5.0 | 5.0 | 5.0 | 5.0 | 0.0 | 5.0 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.30 | 0.30 | 0.30 | 0.30 | 0.30 | 0.30 | 0.30 | 0.30 | 0.30 |

Sun Cream

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Cetearyl glucoside | 4.0 | 4.0 | 4.0 | 4.0 | 4.0 | 4.0 | 4.0 | 4.0 | 4.0 |
| | Dicaprylyl Carbonate | 8.0 | 0.0 | 0.0 | 0.0 | 0.0 | 0.0 | 0.0 | 0.0 | 0.0 |
| | New UV filter | | 3.0 | 15.0 | 5.0 | 10.0 | 5.0 | 8.0 | 5.0 | 15.0 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| Part B | Water | Qs to 100 | Qs to 100 | Qs to 100 | Qs to 100 | Qs to 100 | Qs to 100 | Qs to 100 | Qs to 100 | Qs to 100 |
| | Disodium EDTA | 0.20 | 0.20 | 0.20 | 0.20 | 0.20 | 0.20 | 0.20 | 0.20 | 0.20 |
| | Glycerin | 6.0 | 6.0 | 6.0 | 6.0 | 6.0 | 6.0 | 6.0 | 6.0 | 6.0 |
| | PVP/dimethylconylacrylate/polycarbamyl/polyglycol ester | 3.0 | 3.0 | 3.0 | 3.0 | 3.0 | 3.0 | 3.0 | 3.0 | 3.0 |
| | UV WAT | | 5.0 | 5.0 | 5.0 | 5.0 | 5.0 | 5.0 | 0.0 | 5.0 |
| | Sodium polyacrylate | 0.70 | 0.70 | 0.70 | 0.70 | 0.70 | 0.70 | 0.70 | 0.70 | 0.70 |
| Part C | Dimethicone | 3.0 | 3.0 | 3.0 | 3.0 | 3.0 | 3.0 | 3.0 | 3.0 | 3.0 |
| | Corn Starch modified | 3.0 | 3.0 | 3.0 | 3.0 | 3.0 | 3.0 | 3.0 | 3.0 | 3.0 |
| Part E | Phenoxyethanol (and) Methylparaben (and) Ethylparaben (and) Butylparaben (and) Propylparaben (and) Isobutylparaben | 1.0 | 1.0 | 1.0 | 1.0 | 1.0 | 1.0 | 1.0 | 1.0 | 1.0 |

Sunscreen Gel

| INCI-Name | A % w/w | B % w/w | C % w/w | D % w/w | E % w/w | F % w/w | G % w/w | H % w/w | I % w/w |
|---|---|---|---|---|---|---|---|---|---|
| Alcohol Denatured | Qs to 100 | Qs to 100 | Qs to 100 | Qs to 100 | Qs to 100 | Qs to 100 | Qs to 100 | Qs to 100 | Qs to 100 |
| Hydroxypropyl Cellulose | 1.0 | 1.0 | 1.0 | 1.0 | 1.0 | 1.0 | 1.0 | 1.0 | 1.0 |
| Acrylates/Octylacrylamide Copolymer | 1.0 | 1.0 | 1.0 | 1.0 | 1.0 | 1.0 | 1.0 | 1.0 | 1.0 |
| C12-15 Alkyl Benzoate | 10.0 | 0.0 | 0.0 | 0.0 | 0.0 | 0.0 | 0.0 | 0.0 | 0.0 |
| New UV filter | | 3.0 | 15.0 | 5.0 | 10.0 | 5.0 | 8.0 | 5.0 | 15.0 |
| Cyclotetrasiloxane (and) Cyclopentasiloxane | 3.0 | 3.0 | 3.0 | 3.0 | 3.0 | 3.0 | 3.0 | 3.0 | 3.0 |
| PEG/PPG-4/12 Dimethicone | 1.0 | 1.0 | 1.0 | 1.0 | 1.0 | 1.0 | 1.0 | 1.0 | 1.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| UV WAT | | 5.0 | 5.0 | 5.0 | 5.0 | 5.0 | 5.0 | 0.0 | 5.0 |

Gel Cream

| INCI-Name | A % w/w | B % w/w | C % w/w | D % w/w | E % w/w | F % w/w | G % w/w | H % w/w | I % w/w |
|---|---|---|---|---|---|---|---|---|---|
| Sodium Carbomer | 0.50 | 0.50 | 0.50 | 0.50 | 0.50 | 0.50 | 0.50 | 0.50 | 0.50 |
| Acrylates/C10-C30 Alkyl Acrylate | 1.0 | 1.0 | 1.0 | 1.0 | 1.0 | 1.0 | 1.0 | 1.0 | 1.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| UV WAT | | 5.0 | 5.0 | 5.0 | 5.0 | 5.0 | 5.0 | 0.0 | 5.0 |
| C12-15 Alkyl Benzoate | 2.0 | 0.0 | 0.0 | 0.0 | 0.0 | 0.0 | 0.0 | 0.0 | 0.0 |
| New UV filter | | 3.0 | 15.0 | 5.0 | 10.0 | 5.0 | 8.0 | 5.0 | 15.0 |
| Butylenglycol Dicaprylat/Dicaprate | 4.0 | 0.0 | 0.0 | 0.0 | 0.0 | 0.0 | 0.0 | 0.0 | 0.0 |
| Cetyl Dimethicone | 2.0 | 2.0 | 2.0 | 2.0 | 2.0 | 2.0 | 2.0 | 2.0 | 2.0 |
| Glycerine | 0.50 | 0.50 | 0.50 | 0.50 | 0.50 | 0.50 | 0.50 | 0.50 | 0.50 |
| Tocopherol | 3.0 | 3.0 | 3.0 | 3.0 | 3.0 | 3.0 | 3.0 | 3.0 | 3.0 |
| Methylparabene | 1.0 | 1.0 | 1.0 | 1.0 | 1.0 | 1.0 | 1.0 | 1.0 | 1.0 |
| Phenoxyethanol | 1.0 | 1.0 | 1.0 | 1.0 | 1.0 | 1.0 | 1.0 | 1.0 | 1.0 |

-continued

| | Gel Cream | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Water | ad 100 | ad 100 | ad 100 | ad 100 | ad 100 | ad 100 | ad 100 | ad 100 | ad 100 |

| | Emulsifier Free | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Acrylates/C10-30 Alkyl Acrylate Crosspolymer | 0.40 | 0.40 | 0.40 | 0.40 | 0.40 | 0.40 | 0.40 | 0.40 | 0.40 |
| Xanthan Gum | 0.10 | 0.10 | 0.10 | 0.10 | 0.10 | 0.10 | 0.10 | 0.10 | 0.10 |
| UV SOL | | 10.0 | 15.0 | 5.0 | 10.0 | 5.0 | 8.0 | 5.0 | 15.0 |
| UV LIQ | | 5.0 | 10.0 | 5.0 | 10.0 | 5.0 | 10.0 | 5.0 | 5.0 |
| UV WAT | | 5.0 | 5.0 | 10.0 | 10.0 | 15.0 | 15.0 | 15.0 | 0.0 |
| New UV filter | | 3.0 | 5.0 | 5.0 | 5.0 | 5.0 | 5.0 | 0.0 | 5.0 |
| C12-15 Alkyl Benzoate | 6.0 | 0.0 | 0.0 | 0.0 | 0.0 | 0.0 | 0.0 | 0.0 | 0.0 |
| Octyldodecanol | 7.0 | 0.0 | 0.0 | 0.0 | 0.0 | 0.0 | 0.0 | 0.0 | 0.0 |
| Cetyl Dimethicone | 6.0 | 6.0 | 6.0 | 6.0 | 6.0 | 6.0 | 6.0 | 6.0 | 6.0 |
| Ethylhexyloxyglycerine | 1.0 | 1.0 | 1.0 | 1.0 | 1.0 | 1.0 | 1.0 | 1.0 | 1.0 |
| Butylen Glycol | 10.0 | 10.0 | 10.0 | 10.0 | 10.0 | 10.0 | 10.0 | 10.0 | 10.0 |
| *Glycinc Soja* | 1.0 | 1.0 | 1.0 | 1.0 | 1.0 | 1.0 | 1.0 | 1.0 | 1.0 |
| Vitamin E Acetate | 0.25 | 0.25 | 0.25 | 0.25 | 0.25 | 0.25 | 0.25 | 0.25 | 0.25 |
| Trisodium EDTA | 0.10 | 0.10 | 0.10 | 0.10 | 0.10 | 0.10 | 0.10 | 0.10 | 0.10 |
| Ethanol | 3.50 | 3.50 | 3.50 | 3.50 | 3.50 | 3.50 | 3.50 | 3.50 | 3.50 |
| Parfume | 0.20 | 0.20 | 0.20 | 0.20 | 0.20 | 0.20 | 0.20 | 0.20 | 0.20 |
| Watersoluble Dyes | 0.02 | 0.02 | 0.02 | 0.02 | 0.02 | 0.02 | 0.02 | 0.02 | 0.02 |
| Water | ad 100 | ad 100 | ad 100 | ad 100 | ad 100 | ad 100 | ad 100 | ad 100 | ad 100 |

| | | Sun Spray | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | Ethyl Trisiloxane | 2.50 | 2.50 | 2.50 | 2.50 | 2.50 | 2.50 | 2.50 | 2.50 | 2.50 |
| | Hydrogenated Coco-glycerides | 1.50 | 1.50 | 1.50 | 1.50 | 1.50 | 1.50 | 1.50 | 1.50 | 1.50 |
| | C12-15 Alkyl Benzoate | 3.60 | 3.60 | 3.60 | 3.60 | 3.60 | 3.60 | 3.60 | 3.60 | 3.60 |
| | New UV filter | | 5.0 | 3.0 | 5.0 | 5.0 | 5.0 | 5.0 | 0.0 | 5.0 |
| | UV SOL | | 10.0 | 15.0 | 5.0 | 10.0 | 5.0 | 8.0 | 5.0 | 15.0 |
| | UV LIQ | | 5.0 | 10.0 | 5.0 | 10.0 | 5.0 | 10.0 | 5.0 | 5.0 |
| Part B | Water (and) Caprylic/Capric Triglyceride (and) Glycerin (and) Ceteareth-25 (and) Disodium Ethylene Di(Cocamide PEG-15 Disulfate) (and) Sodium Lauroyl Lactylate (and) Behenyl Alcohol (and) Glyceryl Stearate (and) Glyceryl Stearate Citrate (and) Xanthan Gum | 10.0 | 10.0 | 10.0 | 10.0 | 10.0 | 10.0 | 10.0 | 10.0 | 10.0 |
| | PVP/Hexadecene Copolymer | 0.50 | 0.50 | 0.50 | 0.50 | 0.50 | 0.50 | 0.50 | 0.50 | 0.50 |
| | Aqua | Qs to 10 | Qs to 10 | Qs to 10 | Qs to 10 | Qs to 10 | Qs to 10 | Qs to 10 | Qs to 10 | Qs to 10 |
| | Glycerin | 3.0 | 3.0 | 3.0 | 3.0 | 3.0 | 3.0 | 3.0 | 3.0 | 3.0 |
| | UV WAT | | 5.0 | 5.0 | 10.0 | 10.0 | 15.0 | 15.0 | 15.0 | 0.0 |
| Part C | Alcohol Denatured | 7.0 | 7.0 | 7.0 | 7.0 | 7.0 | 7.0 | 7.0 | 7.0 | 7.0 |
| Part D | Phenoxyethanol (and) Methylparaben (and) Ethylparaben (and) Butylparaben (and) | 0.70 | 0.70 | 0.70 | 0.70 | 0.70 | 0.70 | 0.70 | 0.70 | 0.70 |

-continued

| | Sun Spray | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Propylparaben (and) Isobutylparaben | | | | | | | | | |
| Tocopheryl Acetate | 0.60 | 0.60 | 0.60 | 0.60 | 0.60 | 0.60 | 0.60 | 0.60 | 0.60 |

| | | Sun spray foaming | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | Behenyl Alcohol (and) Glyceryl Stearate (and) Glyceryl Stearate Citrate (and) Disodium Ethylene Di(Cocamide PEG-15 Disulfate) | 0.50 | 0.50 | 0.50 | 0.50 | 0.50 | 0.50 | 0.50 | 0.50 | 0.50 |
| | Isotrideceth-12 | 0.50 | 0.50 | 0.50 | 0.50 | 0.50 | 0.50 | 0.50 | 0.50 | 0.50 |
| | Hydrogenated Cocoglycerides | 1.50 | 0.0 | 0.0 | 0.0 | 0.0 | 0.0 | 0.0 | 0.0 | 0.0 |
| | C12-15 Alkyl Benzoate | 8.0 | 0.0 | 0.0 | 0.0 | 0.0 | 0.0 | 0.0 | 0.0 | 0.0 |
| | New UV filter | | 5.0 | 5.0 | 5.0 | 5.0 | 5.0 | 5.0 | 0.0 | 5.0 |
| | UV SOL | | 3.0 | 15.0 | 5.0 | 10.0 | 5.0 | 8.0 | 5.0 | 15.0 |
| | UV LIQ | | 5.0 | 10.0 | 5.0 | 10.0 | 5.0 | 10.0 | 5.0 | 5.0 |
| Part B | Aqua | 5.0 | 5.0 | 5.0 | 5.0 | 5.0 | 5.0 | 5.0 | 5.0 | 5.0 |
| | Glycerin | 4.0 | 4.0 | 4.0 | 4.0 | 4.0 | 4.0 | 4.0 | 4.0 | 4.0 |
| | Galactoarabinan | 0.25 | 0.25 | 0.25 | 0.25 | 0.25 | 0.25 | 0.25 | 0.25 | 0.25 |
| | UV WAT | | 5.0 | 5.0 | 10.0 | 10.0 | 15.0 | 15.0 | 15.0 | 0.0 |
| Part C | Disodium Ethylene Di(Cocamide PEG-15 Disulfate) (and) Sodium Lauroyl Lactylate | 1.0 | 1.0 | 1.0 | 1.0 | 1.0 | 1.0 | 1.0 | 1.0 | 1.0 |
| | Water | Qs to 100 | Qs to 100 | Qs to 100 | Qs to 100 | Qs to 100 | Qs to 100 | Qs to 100 | Qs to 100 | Qs to 100 |
| Part D | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |

| | Active Naturals Continuous Spray | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Acrylates/Octylacrylamide Copolymer | 3.0 | 3.01 | 3.02 | 3.03 | 3.04 | 3.05 | 3.06 | 3.07 | 3.08 |
| Ascorbyl Palmitate | 0.30 | 0.31 | 0.32 | 0.33 | 0.34 | 0.35 | 0.36 | 0.37 | 0.38 |
| Diisopropyl Adipate | 3.0 | 0.0 | 0.0 | 0.0 | 0.0 | 0.0 | 0.0 | 0.0 | 0.0 |
| Glycerine soja seed extract soybean | 3.0 | 0.0 | 0.0 | 0.0 | 0.0 | 0.0 | 0.0 | 0.0 | 0.0 |
| Isodecyl Neopentanoate | 2.50 | 0.0 | 0.0 | 0.0 | 0.0 | 0.0 | 0.0 | 0.0 | 0.0 |
| New UV filter | | 3.0 | 15.0 | 5.0 | 10.0 | 5.0 | 8.0 | 5.0 | 15.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| UV WAT | | 5.0 | 5.0 | 5.0 | 5.0 | 5.0 | 5.0 | 0.0 | 5.0 |
| Lauryl Lactate | 1.50 | 1.50 | 1.50 | 1.50 | 1.50 | 1.50 | 1.50 | 1.50 | 1.50 |
| PPG-12/SMDI Copolymer | 1.0 | 1.0 | 1.0 | 1.0 | 1.0 | 1.0 | 1.0 | 1.0 | 1.0 |
| Retinyl Palmitate | 0.30 | 0.30 | 0.30 | 0.30 | 0.30 | 0.30 | 0.30 | 0.30 | 0.30 |
| SD Alcohol 40 | 80% V/V | 80% V/V | 80% V/V | 80% V/V | 80% V/V | 80% V/V | 80% V/V | 80% V/V | 80% V/V |
| Tocopherol Acetate | 1.0 | 1.0 | 1.0 | 1.0 | 1.0 | 1.0 | 1.0 | 1.0 | 1.0 |
| Parfume | q.s. | q.s. | q.s. | q.s. | q.s. | q.s. | q.s. | q.s. | q.s. |

-continued

Active Naturals Continuous Spray

| INCI-Name | A % w/w | B % w/w | C % w/w | D % w/w | E % w/w | F % w/w | G % w/w | H % w/w | I % w/w |
|---|---|---|---|---|---|---|---|---|---|
| Aqua | ad 100 | ad 100 | ad 100 | ad 100 | ad 100 | ad 100 | ad 100 | ad 100 | ad 100 |
| Propellent | Qs | Qs | Qs | Qs | Qs | Qs | Qs | Qs | Qs |

W/O Sunscreen Lotion

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | PEG-7 Hydrogenated Castor Oil | 3.0 | 3.0 | 3.0 | 3.0 | 3.0 | 3.0 | 3.0 | 3.0 | 3.0 |
| | Polyglyceryl-3 Diisostearate | 4.0 | 4.0 | 4.0 | 4.0 | 4.0 | 4.0 | 4.0 | 4.0 | 4.0 |
| | Microcrystalline Wax | 1.0 | 1.0 | 1.0 | 1.0 | 1.0 | 1.0 | 1.0 | 1.0 | 1.0 |
| | Magnesium Stearate | 1.50 | 1.50 | 1.50 | 1.50 | 1.50 | 1.50 | 1.50 | 1.50 | 1.50 |
| | Propylparaben | 0.10 | 0.10 | 0.10 | 0.10 | 0.10 | 0.10 | 0.10 | 0.10 | 0.10 |
| | Mineral Oil | 15.0 | 5.0 | 0.0 | 10.0 | 0.0 | 5.0 | 0.0 | 5.0 | 10.0 |
| | New UV filter | | 3.0 | 15.0 | 5.0 | 10.0 | 5.0 | 5.0 | 5.0 | 15.0 |
| | Octyldodecanol | 8.0 | 0.0 | 0.0 | 0.0 | 0.0 | 0.0 | 0.0 | 0.0 | 0.0 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| Part B | Water | qs to 100 | qs to 100 | qs to 100 | qs to 100 | qs to 100 | qs to 100 | qs to 100 | qs to 100 | qs to 100 |
| | UV WAT | | 5.0 | 5.0 | 5.0 | 5.0 | 5.0 | 5.0 | 0.0 | 5.0 |
| Part C | Water (and) Citric Acid | 0.05 | 0.05 | 0.05 | 0.05 | 0.05 | 0.05 | 0.05 | 0.05 | 0.05 |
| | Methylparaben | 0.15 | 0.15 | 0.15 | 0.15 | 0.15 | 0.15 | 0.15 | 0.15 | 0.15 |
| | Magnesium Sulfate | 0.50 | 0.50 | 0.50 | 0.50 | 0.50 | 0.50 | 0.50 | 0.50 | 0.50 |
| | Fragrance | qs | qs | qs | qs | qs | qs | qs | qs | qs |

W/Si sun cream

| | INCI-Name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclopentasiloxane (and) Dimethicone/Vinyl Dimethicone Crosspolymer | 3.0 | 3.0 | 3.0 | 3.0 | 3.0 | 3.0 | 3.0 | 3.0 | 3.0 |
| | PEG-10 Dimethicone | 0.30 | 0.30 | 0.30 | 0.30 | 0.30 | 0.30 | 0.30 | 0.30 | 0.30 |
| | Polyglyceryl-3 Polydimethyl-siloxyethyl Dimethicone | 4.0 | 4.0 | 4.0 | 4.0 | 4.0 | 4.0 | 4.0 | 4.0 | 4.0 |
| | Dimethicone | 5.0 | 5.0 | 5.0 | 5.0 | 5.0 | 5.0 | 5.0 | 5.0 | 5.0 |
| | Cyclomethicone | 15.0 | 15.0 | 15.0 | 15.0 | 15.0 | 15.0 | 15.0 | 15.0 | 15.0 |
| | New UV filter | | 3.0 | 15.0 | 5.0 | 10.0 | 5.0 | 5.0 | 5.0 | 15.0 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| Part C | 1.3-Butylen Glycol | 8.0 | 8.0 | 8.0 | 8.0 | 8.0 | 8.0 | 8.0 | 8.0 | 8.0 |
| | Sodium Citrate | 0.20 | 0.20 | 0.20 | 0.20 | 0.20 | 0.20 | 0.20 | 0.20 | 0.20 |
| | Ethyl Alcohol | 5.0 | 5.0 | 5.0 | 5.0 | 5.0 | 5.0 | 5.0 | 5.0 | 5.0 |
| | Sodium Chloride | 0.50 | 0.50 | 0.50 | 0.50 | 0.50 | 0.50 | 0.50 | 0.50 | 0.50 |
| | UV WAT | | 5.0 | 5.0 | 5.0 | 5.0 | 5.0 | 5.0 | 0.0 | 5.0 |
| | Aqua | Qs to 100 | Qs to 100 | Qs to 100 | Qs to 100 | Qs to 100 | Qs to 100 | Qs to 100 | Qs to 100 | Qs to 100 |

Lipstick

| INCI-Name | A % w/w | B % w/w | C % w/w | D % w/w | E % w/w | F % w/w | G % w/w | H % w/w | I % w/w |
|---|---|---|---|---|---|---|---|---|---|
| Caprylic/Capric Triglyceride | 12.00 | 0.0 | 0.0 | 0.0 | 0.0 | 0.0 | 0.0 | 0.0 | 0.0 |
| New UV filter | | 3.0 | 15.0 | 5.0 | 10.0 | 5.0 | 5.0 | 5.0 | 15.0 |

-continued

| INCI-Name | Lipstick | | | | | | | | |
|---|---|---|---|---|---|---|---|---|---|
| | A % w/w | B % w/w | C % w/w | D % w/w | E % w/w | F % w/w | G % w/w | H % w/w | I % w/w |
| Octyldodecanol | 7.0 | 7.0 | 7.0 | 7.0 | 7.0 | 7.0 | 7.0 | 7.0 | 7.0 |
| Pentaerythrityl Tetraisostearate | 10.0 | 5.0 | 0.0 | 5.0 | 0.0 | 0.0 | 0.0 | 0.0 | 5.0 |
| Polyglyceryl-3 Diisostearate | 2.50 | 2.50 | 2.50 | 2.50 | 2.50 | 2.50 | 2.50 | 2.50 | 2.50 |
| Bis-Diglyceryl Polyacyladipate-2 | 9.0 | 9.0 | 9.0 | 9.0 | 9.0 | 9.0 | 9.0 | 9.0 | 9.0 |
| Cetearyl Alcohol | 8.0 | 8.0 | 8.0 | 8.0 | 8.0 | 8.0 | 8.0 | 8.0 | 8.0 |
| Myristyl Myristate | 3.50 | 3.50 | 3.50 | 3.50 | 3.50 | 3.50 | 3.50 | 3.50 | 3.50 |
| Beeswax | 5.0 | 5.0 | 5.0 | 5.0 | 5.0 | 5.0 | 5.0 | 5.0 | 5.0 |
| *Copernicia Cerifera* (Carnauba) Wax | 1.50 | 1.50 | 1.50 | 1.50 | 1.50 | 1.50 | 1.50 | 1.50 | 1.50 |
| Cera Alba | 0.50 | 0.50 | 0.50 | 0.50 | 0.50 | 0.50 | 0.50 | 0.50 | 0.50 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| Tocopheryl Acetate | 0.50 | 0.50 | 0.50 | 0.50 | 0.50 | 0.50 | 0.50 | 0.50 | 0.50 |
| Tocopherol; Ascorbyl Palmitate | 0.05 | 0.05 | 0.05 | 0.05 | 0.05 | 0.05 | 0.05 | 0.05 | 0.05 |
| *Simmondsia Chinensis* (Jojoba) Seed Extract | 2.0 | 2.0 | 2.0 | 2.0 | 2.0 | 2.0 | 2.0 | 2.0 | 2.0 |
| Parfum. BHT | q.s | q.s | q.s | q.s | q.s | q.s | q.s | q.s | q.s |
| *Ricinus Communis* | QS to 100 | QS to 100 | QS to 100 | QS to 100 | QS to 100 | QS to 100 | QS to 100 | QS to 100 | QS to 100 |

| INCI-Name | Waterproof Gel | | | | | | | | |
|---|---|---|---|---|---|---|---|---|---|
| | A % w/w | B % w/w | C % w/w | D % w/w | E % w/w | F % w/w | G % w/w | H % w/w | I % w/w |
| Anhydrous Ethanol | Qsp 100 | Qsp 100 | Qsp 100 | Qsp 100 | Qsp 100 | Qsp 100 | Qsp 100 | Qsp 100 | Qsp 100 |
| Hydroxypropyl Cellulose | 1.0 | 1.0 | 1.0 | 1.0 | 1.0 | 1.0 | 1.0 | 1.0 | 1.0 |
| Acrylates/Octylacrylamide Copolymer | 1.0 | 1.0 | 1.0 | 1.0 | 1.0 | 1.0 | 1.0 | 1.0 | 1.0 |
| New UV filter | | 3.0 | 15.0 | 5.0 | 10.0 | 5.0 | 5.0 | 5.0 | 15.0 |
| C12-15 Alkyl Benzoate | 10.0 | 10.0 | 10.0 | 10.0 | 10.0 | 10.0 | 10.0 | 10.0 | 10.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| Cyclomethicone | 3.0 | 3.0 | 3.0 | 3.0 | 3.0 | 3.0 | 3.0 | 3.0 | 3.0 |
| PEG/PPG-4/12 Dimethicone | 1.0 | 1.0 | 1.0 | 1.0 | 1.0 | 1.0 | 1.0 | 1.0 | 1.0 |

| INCI-Name | SUNSCREEN Oleogel | | | | | | | | |
|---|---|---|---|---|---|---|---|---|---|
| | A % w/w | B % w/w | C % w/w | D % w/w | E % w/w | F % w/w | G % w/w | H % w/w | I % w/w |
| Isopropyl Myristate | 38.0 | qs. 100 | qs. 100 | qs. 100 | qs. 100 | qs. 100 | qs. 100 | qs. 100 | qs. 100 |
| C12-15 Alkyl Benzoate | 10.0 | 5.0 | 5.0 | 5.0 | 5.0 | 5.0 | 5.0 | 5.0 | 5.0 |
| New UV filter | | 3.0 | 15.0 | 5.0 | 10.0 | 5.0 | 5.0 | 5.0 | 15.0 |
| Caprylic/Capric Triglyceride | 39.0 | 15.0 | 15.0 | 15.0 | 15.0 | 15.0 | 15.0 | 15.0 | 15.0 |
| Perfume | q.s. | q.s. | q.s. | q.s. | q.s. | q.s. | q.s. | q.s. | q.s. |
| Disteardimonium Hectorite | 15.0 | 15.0 | 15.0 | 15.0 | 15.0 | 15.0 | 15.0 | 15.0 | 15.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| Propylene Carbonate | 5.0 | 5.0 | 5.0 | 5.0 | 5.0 | 5.0 | 5.0 | 5.0 | 5.0 |

| | O/W/O Soft Cream | | | | | | | | |
|---|---|---|---|---|---|---|---|---|---|
| | | A % w/w | B % w/w | C % w/w | D % w/w | E % w/w | F % w/w | G % w/w | H % w/w | I % w/w |
| | INCI-Name | | | | | | | | | |
| Part A | PEG-60 Hydrogenated Castor Oil | 0.40 | 0.40 | 0.40 | 0.40 | 0.40 | 0.40 | 0.40 | 0.40 | 0.40 |
| | Water | 0.90 | 0.90 | 0.90 | 0.90 | 0.90 | 0.90 | 0.90 | 0.90 | 0.90 |
| Part B | Tocopheryl Acetate | 2.0 | 2.0 | 2.0 | 2.0 | 2.0 | 2.0 | 2.0 | 2.0 | 2.0 |
| | Retinyl Palmitate | 0.50 | 0.50 | 0.50 | 0.50 | 0.50 | 0.50 | 0.50 | 0.50 | 0.50 |
| | Caprylic/Capric Triglyceride | 2.50 | 2.50 | 2.50 | 2.50 | 2.50 | 2.50 | 2.50 | 2.50 | 2.50 |
| Part C | Water | Qs to 100 | Qs to 100 | Qs to 100 | Qs to 100 | Qs to 100 | Qs to 100 | Qs to 100 | Qs to 100 | Qs to 100 |
| | Sodium Chloride | 0.40 | 0.40 | 0.40 | 0.40 | 0.40 | 0.40 | 0.40 | 0.40 | 0.40 |
| | UV WAT | | 5.0 | 5.0 | 5.0 | 5.0 | 5.0 | 5.0 | 0.0 | 5.0 |
| Part D | Cetyl PEG/PPG-10/1 Dimethicone | 2.0 | 2.0 | 2.0 | 2.0 | 2.0 | 2.0 | 2.0 | 2.0 | 2.0 |
| | Microcrystalline Wax | 0.90 | 0.90 | 0.90 | 0.90 | 0.90 | 0.90 | 0.90 | 0.90 | 0.90 |
| | Hydrogenated Castor Oil | 0.60 | 0.60 | 0.60 | 0.60 | 0.60 | 0.60 | 0.60 | 0.60 | 0.60 |
| | Decyl Oleate | 10.5 | 5.0 | 5.0 | 5.0 | 5.0 | 5.0 | 5.0 | 5.0 | 5.0 |
| | Caprylic/Capric Triglyceride | 10.0 | 0.0 | 0.0 | 0.0 | 0.0 | 0.0 | 0.0 | 0.0 | 0.0 |
| | Jojoba (*Buxus Chinensis*) Oil | 2.0 | 2.0 | 2.0 | 2.0 | 2.0 | 2.0 | 2.0 | 2.0 | 2.0 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| | New UV filter | | 3.0 | 15.0 | 5.0 | 10.0 | 5.0 | 5.0 | 5.0 | 15.0 |
| | Preservative, Parfum | q.s. | q.s. | q.s. | q.s. | q.s. | q.s. | q.s. | q.s. | q.s. |

| | W/O/W Emulsion | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Glycerylstearate | 3.0 | 3.0 | 3.0 | 3.0 | 3.0 | 3.0 | 3.0 | 3.0 | 3.0 |
| PEG-100-Stearate | 0.75 | 0.75 | 0.75 | 0.75 | 0.75 | 0.75 | 0.75 | 0.75 | 0.75 |
| Behenylalcohol | 2.0 | 2.0 | 2.0 | 2.0 | 2.0 | 2.0 | 2.0 | 2.0 | 2.0 |
| Caprylic-/Capric-Triglyceride | 8.0 | 0.0 | 0.0 | 0.0 | 0.0 | 0.0 | 0.0 | 0.0 | 0.0 |
| Octyldodecanol | 5.0 | 0.0 | 0.0 | 0.0 | 0.0 | 0.0 | 0.0 | 0.0 | 0.0 |
| C12-15 Alkylbenzoate | 3.0 | 0.0 | 0.0 | 0.0 | 0.0 | 0.0 | 0.0 | 0.0 | 0.0 |
| New UV filter | | 3.0 | 15.0 | 5.0 | 10.0 | 5.0 | 5.0 | 5.0 | 15.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| UV WAT | | 5.0 | 5.0 | 5.0 | 5.0 | 5.0 | 5.0 | 0.0 | 5.0 |
| Dodecanedioic Acid | 1.0 | 1.0 | 1.0 | 1.0 | 1.0 | 1.0 | 1.0 | 1.0 | 1.0 |
| Magnesium Sulfate | 0.80 | 0.80 | 0.80 | 0.80 | 0.80 | 0.80 | 0.80 | 0.80 | 0.80 |
| EDTA | 0.10 | 0.10 | 0.10 | 0.10 | 0.10 | 0.10 | 0.10 | 0.10 | 0.10 |
| Phenoxyethanol | q.s. | q.s. | q.s. | q.s. | q.s. | q.s. | q.s. | q.s. | q.s. |
| Parfume | q.s. | q.s. | q.s. | q.s. | q.s. | q.s. | q.s. | q.s. | q.s. |
| Water | ad 100 | ad 10.0 | ad 100 | ad 100 | ad 100 | ad 100 | ad 100 | ad 100 | ad 100 |
| PH-value adjusted to 6.0 | | | | | | | | | |

| | Cream-to-powder | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| Isoeicosane | 10.0 | 5.0 | 5.0 | 5.0 | 5.0 | 5.0 | 5.0 | 5.0 | 5.0 |
| Polyisobutene | 2.0 | 2.0 | 2.0 | 2.0 | 2.0 | 2.0 | 2.0 | 2.0 | 2.0 |
| New UV filter | | 3.0 | 15.0 | 5.0 | 10.0 | 5.0 | 5.0 | 5.0 | 15.0 |
| Cetearyl Octanoate | 20.5 | 10.0 | 5.0 | 10.0 | 5.0 | 5.0 | 5.0 | 5.0 | 10.0 |
| Oleyl alcohol | 5.0 | 5.0 | 5.0 | 5.0 | 5.0 | 5.0 | 5.0 | 5.0 | 5.0 |
| Ceresin | 4.50 | 4.50 | 4.50 | 4.50 | 4.50 | 4.50 | 4.50 | 4.50 | 4.50 |
| Talc | 11.60 | 11.60 | 11.60 | 11.60 | 11.60 | 11.60 | 11.60 | 11.60 | 11.60 |
| Polyethylene | 4.0 | 4.0 | 4.0 | 4.0 | 4.0 | 4.0 | 4.0 | 4.0 | 4.0 |

Cream-to-powder

| INCI-Name | A % w/w | B % w/w | C % w/w | D % w/w | E % w/w | F % w/w | G % w/w | H % w/w | I % w/w |
|---|---|---|---|---|---|---|---|---|---|
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| Silica | 17.75 | 17.75 | 17.75 | 17.75 | 17.75 | 17.75 | 17.75 | 17.75 | 17.75 |
| Calcium Aluminum Borosilicate (and) Bismuth oxychloride | 1.0 | 1.0 | 1.0 | 1.0 | 1.0 | 1.0 | 1.0 | 1.0 | 1.0 |
| Iron Oxides | 3.40 | 3.40 | 3.40 | 3.40 | 3.40 | 3.40 | 3.40 | 3.40 | 3.40 |
| Tocopherol Acetate | 0.25 | 0.25 | 0.25 | 0.25 | 0.25 | 0.25 | 0.25 | 0.25 | 0.25 |

Foundations: Anhydrous forms

| INCI-Name | A % w/w | B % w/w | C % w/w | D % w/w | E % w/w | F % w/w | G % w/w | H % w/w | I % w/w |
|---|---|---|---|---|---|---|---|---|---|
| Isononyl Isononanoate | qsp | qsp | qsp | qsp | qsp | qsp | qsp | qsp | qsp |
| New UV filter | 3.0 | 3.0 | 15.0 | 5.0 | 10.0 | 5.0 | 5.0 | 5.0 | 15.0 |
| Sorbitan Sesquioleate | 0.50 | 0.50 | 0.50 | 0.50 | 0.50 | 0.50 | 0.50 | 0.50 | 0.50 |
| Cyclopentasiloxane | 15.0 | 15.0 | 15.0 | 15.0 | 15.0 | 15.0 | 15.0 | 15.0 | 15.0 |
| Cylopentasiloxane (and) Quaternium-18 Hectorite | 15.0 | 15.0 | 15.0 | 15.0 | 15.0 | 15.0 | 15.0 | 15.0 | 15.0 |
| Talc | 5.0 | 5.0 | 5.0 | 5.0 | 5.0 | 5.0 | 5.0 | 5.0 | 5.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| Iron oxides | 2.50 | 2.50 | 2.50 | 2.50 | 2.50 | 2.50 | 2.50 | 2.50 | 2.50 |
| PVP/eicosane copolymer | 1.0 | 1.0 | 1.0 | 1.0 | 1.0 | 1.0 | 1.0 | 1.0 | 1.0 |
| Tocopherol Acetate | 0.50 | 0.50 | 0.50 | 0.50 | 0.50 | 0.50 | 0.50 | 0.50 | 0.50 |

Pickering Emulsions

| INCI-Name | A % w/w | B % w/w | C % w/w | D % w/w | E % w/w | F % w/w | G % w/w | H % w/w | I % w/w |
|---|---|---|---|---|---|---|---|---|---|
| Octyidodecanol | 5.50 | 0.0 | | | | | | | |
| New UV filter | 3.0 | 3.0 | 15.0 | 5.0 | 10.0 | 5.0 | 5.0 | 5.0 | 15.0 |
| C12-15-Alkyl Benzoate | 6.50 | 0.0 | 0.0 | 0.0 | 0.0 | 0.0 | 0.0 | 0.0 | 0.0 |
| Dicaprylyl Ether | 5.50 | 0.0 | 0.0 | 0.0 | 0.0 | 0.0 | 0.0 | 0.0 | 0.0 |
| Hydroxyoctacosanyl Hydroxystearate | 2.0 | 2.0 | 2.0 | 2.0 | 2.0 | 2.0 | 2.0 | 2.0 | 2.0 |
| Disteardimonium Hectorit | 1.0 | 1.0 | 1.0 | 1.0 | 1.0 | 1.0 | 1.0 | 1.0 | 1.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| UV WAT | | 5.0 | 5.0 | 5.0 | 5.0 | 5.0 | 5.0 | 0.0 | 5.0 |
| Bariumsulfate | 0.50 | 0.50 | 0.50 | 0.50 | 0.50 | 0.50 | 0.50 | 0.50 | 0.50 |
| Boron Nitride | 2.0 | 2.0 | 2.0 | 2.0 | 2.0 | 2.0 | 2.0 | 2.0 | 2.0 |
| NaCl | 1.0 | 1.0 | 1.0 | 1.0 | 1.0 | 1.0 | 1.0 | 1.0 | 1.0 |
| Glycerine | 10.0 | 10.0 | 10.0 | 10.0 | 10.0 | 10.0 | 10.0 | 10.0 | 10.0 |
| Trisodium EDTA | 1.0 | 1.0 | 1.0 | 1.0 | 1.0 | 1.0 | 1.0 | 1.0 | 1.0 |
| Porpylene Carbonate | 0.33 | 0.33 | 0.33 | 0.33 | 0.33 | 0.33 | 0.33 | 0.33 | 0.33 |
| Methylparabene | 0.20 | 0.20 | 0.20 | 0.20 | 0.20 | 0.20 | 0.20 | 0.20 | 0.20 |
| Phenoxyethanol | 0.50 | 0.50 | 0.50 | 0.50 | 0.50 | 0.50 | 0.50 | 0.50 | 0.50 |
| Hexamidine Diisethionate | 0.08 | 0.08 | 0.08 | 0.08 | 0.08 | 0.08 | 0.08 | 0.08 | 0.08 |
| Parfume | 0.40 | 0.40 | 0.40 | 0.40 | 0.40 | 0.40 | 0.40 | 0.40 | 0.40 |
| Water | ad 100 | ad 100 | ad 100 | ad 100 | ad 100 | ad 100 | ad 100 | ad 100 | ad 100 |

| Microemulsion Lotion | | | | | | | | | |
|---|---|---|---|---|---|---|---|---|---|
| INCI-Name | A % w/w | B % w/w | C % w/w | D % w/w | E % w/w | F % w/w | G % w/w | H % w/w | I % w/w |
| PPG-26-Buteth-26 | 3.0 | 3.0 | 3.0 | 3.0 | 3.0 | 3.0 | 3.0 | 3.0 | 3.0 |
| Ceteareth 20 | 10.0 | 10.0 | 10.0 | 10.0 | 10.0 | 10.0 | 10.0 | 10.0 | 10.0 |
| C12-15 Alkyl Benzoate | 5.0 | 0.0 | 0.0 | 0.0 | 0.0 | 0.0 | 0.0 | 0.0 | 0.0 |
| New UV filter | 3.0 | 3.0 | 15.0 | 5.0 | 10.0 | 5.0 | 5.0 | 5.0 | 15.0 |
| Oleth-5 | 4.0 | 4.0 | 4.0 | 4.0 | 4.0 | 4.0 | 4.0 | 4.0 | 4.0 |
| UV SOL | | 5.0 | 10.0 | 5.0 | 10.0 | 5.0 | 10.0 | 5.0 | 5.0 |
| UV LIQ | | 5.0 | 5.0 | 10.0 | 10.0 | 15.0 | 15.0 | 15.0 | 0.0 |
| PPG-11 Stearyl Ether | 10.0 | 0.0 | 0.0 | 0.0 | 0.0 | 0.0 | 0.0 | 0.0 | 0.0 |
| UV WAT | | 5.0 | 5.0 | 5.0 | 5.0 | 5.0 | 5.0 | 0.0 | 5.0 |
| Aluminum Chlorohydrex PG | 15.0 | 15.0 | 15.0 | 15.0 | 15.0 | 15.0 | 15.0 | 15.0 | 15.0 |
| Water | Qs to 100 | Qs to 100 | Qs to 100 | Qs to 100 | Qs to 100 | Qs to 100 | Qs to 100 | Qs to 100 | Qs to 100 |

| | Cationic O/W sun cream | | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | Palmitamidopropyl-trimonium Chloride | 6.0 | 6.0 | 6.0 | 6.0 | 6.0 | 6.0 | 6.0 | 6.0 | 6.0 |
| | Stearyl Alcohol | 2.0 | 2.0 | 2.0 | 2.0 | 2.0 | 2.0 | 2.0 | 2.0 | 2.0 |
| | Isocetyl Palmitate | 4.0 | 0.0 | 0.0 | 0.0 | 0.0 | 0.0 | 0.0 | 0.0 | 0.0 |
| | Decyl Cocoate | 3.0 | 0.0 | 0.0 | 0.0 | 0.0 | 0.0 | 0.0 | 0.0 | 0.0 |
| | C12-15 Alkyl Benzoate | 3.0 | 0.0 | 0.0 | 0.0 | 0.0 | 0.0 | 0.0 | 0.0 | 0.0 |
| | New UV filter | 3.0 | 3.0 | 15.0 | 5.0 | 10.0 | 5.0 | 5.0 | 5.0 | 15.0 |
| | Cetyl Dimethicone | 0.75 | 0.75 | 0.75 | 0.75 | 0.75 | 0.75 | 0.75 | 0.75 | 0.75 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |
| Part B | Aqua | Qs to 100 | Qs to 100 | Qs to 100 | Qs to 100 | Qs to 100 | Qs to 100 | Qs to 100 | Qs to 100 | Qs to 100 |
| | Glycerin | 3.0 | 3.0 | 3.0 | 3.0 | 3.0 | 3.0 | 3.0 | 3.0 | 3.0 |
| | Trisodium EDTA | 0.10 | 0.10 | 0.10 | 0.10 | 0.10 | 0.10 | 0.10 | 0.10 | 0.10 |
| | UV WAT | | 5.0 | 5.0 | 5.0 | 5.0 | 5.0 | 5.0 | 0.0 | 5.0 |
| Part C | Capryl/Capramidopropyl Betaine | 8.0 | 8.0 | 8.0 | 8.0 | 8.0 | 8.0 | 8.0 | 8.0 | 8.0 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.80 | 0.80 | 0.80 | 0.80 | 0.80 | 0.80 | 0.80 | 0.80 | 0.80 |

| | Si/W sun cream | | | | | | | | | |
|---|---|---|---|---|---|---|---|---|---|---|
| | INCI-Name | A % w/w | B % w/w | C % w/w | D % w/w | E % w/w | F % w/w | G % w/w | H % w/w | I % w/w |
| Part A | Cyclopentasiloxane (and) Dimethicone/Vinyl Dimethicone Crosspolymer | 2.0 | 2.0 | 2.0 | 2.0 | 2.0 | 2.0 | 2.0 | 2.0 | 2.0 |
| | Dimethicone (and) Di-methicone/Vinyl Dimethicone Crosspolymer | 3.0 | 3.0 | 3.0 | 3.0 | 3.0 | 3.0 | 3.0 | 3.0 | 3.0 |
| | Cyclopentasiloxane | 10.0 | 10.0 | 10.0 | 10.0 | 10.0 | 10.0 | 10.0 | 10.0 | 10.0 |
| | New UV filter | 3.0 | 3.0 | 15.0 | 5.0 | 10.0 | 5.0 | 5.0 | 5.0 | 15.0 |
| | UV SOL | | 5.0 | 10.0 | 5.0 | 10.0 | 5.0 | 10.0 | 5.0 | 5.0 |
| | UV LIQ | | 5.0 | 5.0 | 10.0 | 10.0 | 15.0 | 15.0 | 15.0 | 0.0 |

-continued

| | | Si/W sun cream | | | | | | | | |
|---|---|---|---|---|---|---|---|---|---|---|
| | | A | B | C | D | E | F | G | H | I |
| | INCI-Name | % w/w | % w/w | % w/w | % w/w | % w/w | % w/w | % w/w | % w/w | % w/w |
| Part B | 1.3-Butylen Glycol | 3.0 | 3.0 | 3.0 | 3.0 | 3.0 | 3.0 | 3.0 | 3.0 | 3.0 |
| | Polyglyceryl-3 Disiloxane Dimethicone | 0.60 | 0.60 | 0.60 | 0.60 | 0.60 | 0.60 | 0.60 | 0.60 | 0.60 |
| | Polyglyceryl-3 Polydimethylsiloxyethyl Dimethicone | 0.30 | 0.30 | 0.30 | 0.30 | 0.30 | 0.30 | 0.30 | 0.30 | 0.30 |
| | Acrylamide/Sodium Acryloyldimethyltaurate Copolymer (and) Isohexadecane (and) Polysorbate 80 | 0.60 | 0.60 | 0.60 | 0.60 | 0.60 | 0.60 | 0.60 | 0.60 | 0.60 |
| | Ammonium Acryloyldimethyltaurate/VP Copolymer | 0.65 | 0.65 | 0.65 | 0.65 | 0.65 | 0.65 | 0.65 | 0.65 | 0.65 |
| | Sodium Chloride | 0.10 | 0.10 | 0.10 | 0.10 | 0.10 | 0.10 | 0.10 | 0.10 | 0.10 |
| | Aqua | Qs to 100 | Qs to 100 | Qs to 100 | Qs to 100 | Qs to 100 | Qs to 100 | Qs to 100 | Qs to 100 | Qs to 100 |
| | UV WAT | | 5.0 | 5.0 | 5.0 | 5.0 | 5.0 | 5.0 | 0.0 | 5.0 |

The invention relates also to cosmetic compositions that comprise at least one of the UV absorbers according to the invention. The cosmetic compositions are suitable especially as UV filters, that is to say for the protection of organic materials that are sensitive to ultraviolet light, especially skin and hair, against the damaging action of UV radiation.

The UV absorbers can be used either in the dissolved state or in the micronized state.

The cosmetic compositions contain, for example, from 0.1 to 30% by weight, preferably from 0.1 to 15% by weight and especially from 0.5 to 10% by weight, based on the total weight of the composition, of one or more UV absorbers and at least one cosmetically tolerable adjuvant.

The cosmetic compositions can be prepared by physically mixing the UV absorber(s) with the adjuvant using customary methods, for example by simply stirring together the individual components, especially by making use of the dissolution properties of already known cosmetic UV absorbers, for example OMC, salicylic acid isooctyl ester, inter alia. The UV absorber can be used, for example, without further treatment, or in the micronized state, or in the form of a powder.

The cosmetic compositions may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the compositions contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

As oil components of oil-containing compositions (e.g. oils, W/O, O/W, O/W/O and W/O/W emulsions or microemulsions) there come into consideration, for example, Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl)adipate, di(2-ethylhexyl)succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:
addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
$C_{12}$-$C_{22}$ fatty acid mono- and di-esters of addition products of from 1 to 30 mol of ethylene oxide with polyols having from 3 to 6 carbon atoms, especially with glycerol;
glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;
$C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;
addition products of from 2 to 60 mol, especially from 15 to 60 mol, of ethylene oxide with castor oil and/or hydrogenated castor oil;
polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;
partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;
mono-, di- and tri-alkylphosphates and also mono-, di- and/or tri-PEG-alkylphosphates and salts thereof;
wool wax alcohols;
one or more ethoxylated esters of natural derivatives, for example polyethoxylated esters of hydrogenated castor oil;
silicone oil emulsifiers, for example silicone polyol;
polysiloxane/polyalkyl/polyether copolymers and corresponding derivatives, for example cetyl dimethicone copolyol;
mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates and also
polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include mono-glycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxy-ethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group.

Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference being given to those of the esterquat type, preferably methyl-quaternised di-fatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates.

Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinyl-pyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilisers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5 Cl \times 2.5H_2O$, the use of which is especially preferred (see J. Pharm. Pharmacol. 26, 531 (1975)). Besides the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, Ciba Specialty Chemicals Inc.) has also proved especially effective.

As anti-dandruff agents there may be used, for example, climbazole, octopirox and zinc pyrithione. Customary film formers include, for example, chitosan, microcrystalline chitosan, quaternised chitosan, polyvinylpyrrolidone, vinyl pyrrolidone/vinyl acetate copolymers, polymers of quaternary cellulose derivatives containing a high proportion of acrylic acid, collagen, hyaluronic acid and salts thereof and similar compounds. As swelling agents for aqueous phases there may be used montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant kind which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts (e.g. from pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxy-butyrophenone, uric acid and derivatives thereof, mannose and derivatives thereof, superoxide dismutase, N-[3-(3,5-di-tert-butyl-4-hydroxyphenyl)propionyl] sulfanilic acid (and salts thereof, for example the sodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber(s).

To improve the flow behaviour it is also possible to employ hydrotropic agents, for example ethanol, isopropyl alcohol or polyols. The polyols that come into consideration for that purpose have preferably from 2 to 15 carbon atoms and at least two hydroxy groups.

The polyols may also contain further functional groups, especially amino groups, and/or may be modified with nitrogen. Typical examples are as follows:

glycerol;

alkylene glycols, for example ethylene glycol, diethylene glycol, propylene glycol, butylene glycol, hexylene glycol and also polyethylene glycols having an average molecular weight of from 100 to 1000 dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethylolbutane, pentaerythritol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxyethyl isobutyrate, p-tert-butylcyclohexyl acetate, linalyl acetate, dimethyl-benzyl-carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, a-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic compositions to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or α-mercaptoethanesulfonic acid, or oxidising agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone, erythrulose or mixtures of dihydroxyacetone and erythrulose.

Cosmetic formulations according to the invention are contained in a wide variety of cosmetic preparations. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl-dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl-dimethyl-2-hydroxyethylammonium chloride or Quaternium 80 is added;

b) Quat-doped solutions of the UV absorber according to the invention in butyltriglycol and tributyl citrate;

c) mixtures or solutions of the UV absorber according to the invention with n-alkylpyrrolidone.

The cosmetic preparation according to the invention contains from 0.1 to 15% by weight, preferably from 0.5 to 10% by weight, based on the total weight of the composition, of a UV absorber of formula (1) or of a mixture of UV absorbers and a cosmetically tolerable adjuvant.

The cosmetic preparation can be prepared by physically mixing the UV absorber or UV absorbers with the adjuvant using conventional methods, for example by simply stirring the individual components together.

The cosmetic preparation according to the invention can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation.

As a water-in-oil or oil-in-water emulsion, the cosmetically tolerable adjuvant preferably contains from 5 to 50% of an oil phase, from 5 to 20% of an emulsifier and from 30 to 90% water. The oil phase can comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

For the cosmetic preparation according to the invention it is possible to use any conventionally usable emulsifier, for example one or more ethoxylated esters of natural derivatives, for example polyethoxylated esters of hydrogenated castor oil, or a silicone oil emulsifier, for example silicone polyol; an unethoxylated or ethoxylated fatty acid soap; an ethoxylated fatty alcohol; an unethoxylated or ethoxylated sorbitan ester; an ethoxylated fatty acid; or an ethoxylated glyceride.

The cosmetic preparation may also comprise further components, for example emollients, emulsion stabilisers, skin moisturisers, skin-tanning accelerators, thickeners, such as xanthan, moisture retention agents, for example glycerol, preservatives, aromatic substances and colourants.

The cosmetic preparation according to the invention is distinguished by excellent protection of human skin against the damaging effect of sunlight.

The phosphono benzylidene compounds according to the present invention may also be used to stabilize common ingredients of cosmetic formulations as described above. For example, the phosphono benzylidene compounds according to the present invention may be used to stabilize other UV absorbers like the UV-A filter Butyl Methoxydibenzoylmethane (Parsol 1789, CAS No. 70356-09-1).

The phosphono benzylidene compounds according to formula (1) are suitable especially as UV filters for the protection of polymeric materials. The UV filters are preferably used in polymeric substrates as disclosed in WO 2006/058856 on p. 4, l. 20 to p. 10, l. 15.

The polymeric substrates of the present invention comprise for example: polymers of monoolefins and diolefins, and mixtures thereof, copolymers of monoolefins and diolefins with each other or with other vinyl monomers, hydrocarbon resins, polystyrene, aromatic homopolymers and copolymers derived from vinyl aromatic monomers, hydrogenated aromatic polymers derived from hydrogenation of polymers, hydrogenated aromatic polymers derived from hydrogenation of polymers mentioned, graft copolymers of vinyl aromatic monomers, halogen-containing polymers such as, polymers derived from, -unsaturated acids and derivatives thereof, polymers derived from unsaturated alcohols and amines or the acyl derivatives or acetals thereof, homopolymers and copolymers of cyclic ethers, polyacetals, polyphenylene oxides and sulfides, and mixtures of polyphenylene oxides with styrene polymers or polyamides, polyurethanes, polyamides and copolyamides, polyureas, polyimides, polyamide-imides, polyetherimids, polyesterimids, polyhydantoins and polybenzimidazoles, polyesters, polycarbonates and polyester carbonates. polyketones. polysulfones, polyether sulfones and polyether ketones. crosslinked polymers derived from aldehydes on the one hand and phenols, ureas and melamines on the other hand, drying and non-drying alkyd resins. unsaturated polyester resins derived from copolyesters of saturated and unsaturated dicarboxylic acids with polyhydric alcohols and vinyl compounds as crosslinking agents, and also halogen-containing modifications thereof of low flammability, crosslinkable acrylic resins derived from substituted acrylates, for example epoxy acrylates, urethane acrylates or polyester acrylates, alkyd resins, polyester resins and acrylate resins crosslinked with melamine resins, urea resins, isocyanates, isocyanurates, polyisocyanates or epoxy resins, crosslinked epoxy resins derived from aliphatic, cycloaliphatic, heterocyclic or aromatic glycidyl compounds or natural polymers.

The present polymeric substrates are used for example in moldings, rotomolded articles, injection molded articles, blow molded articles, films, tapes, mono-filaments, fibers, nonwovens, profiles, adhesives or putties, surface coatings and the like.

For example, the present PVC applications are employed for construction articles such as roofing and siding. The present polymeric substrates are used in polymer films in automotive windshields, other automotive glass, and in home and office windows.

The benzylidene compounds according to the present invention are also useful for stabilising body-care and household products. in particular used for skin-care products, bath and shower additives, preparations containing fragrances and odoriferous substances, hair-care products, dentifrices, deodorising and antiperspirant preparations, decorative preparations, light protection formulations and preparations containing active ingredients.

The body-care products can be in the form of creams, ointments, pastes, foams, gels, lotions, powders, make-ups, sprays, sticks or aerosols. They preferably contain the benzylidene compounds according to the present invention and, optionally, in admixture with other light stabilisers in the oil phase or in the aqueous or aqueous/alcoholic phase.

The following Table lists typical examples of body-care products of this invention and their ingredients:

| Body-care product | Ingredients |
|---|---|
| moisturising cream | vegetable oil, emulsifier, thickener, perfume, water, UV absorber |
| shampoo | surfactant, emulsifier, preservatives, perfume, UV absorber |
| toothpaste | cleaning agent, thickener, sweetener, flavour, colourant, UV absorber |
| lip-care stick | vegetable oil, wax, $TiO_2$, UV absorber |

Typical examples of novel household cleaning and treating agents are:

| Household cleaners/ household treating agents | Ingredients |
|---|---|
| detergent concentrate | surfactant mixture, ethanol, UV absorber, water |
| shoe polish | wax, wax emulsifier, UV absorber, water, preservative |
| wax-containing floor cleaning agent | emulsifier, wax, sodium chloride, UV absorber, water, preservative |

The benzylidene compounds are usually incorporated by dissolution in an oil phase or alcoholic or water phase, where required at elevated temperature The present invention will be described more specifically with reference to the following Examples, which, however, are not intended to restrict the scope of the invention.

In the following Examples percentages relate to weight. The amounts of the benzylidene compounds used relate to the pure substance.

A. Preparation Examples of Phosphono UV Absorbers
Preparation of Compound (P-1):

Phosphono compound P-1 was synthesized according to method (A) described on page 305 in Tetrahedron, Vol. 30, by W. Lehnert. By using 6.95 grams of para-anisaldehyde and 11.56 grams of triethyl phosphonoacetate the desired product was obtained in yields of 95% (16.32 grams) as a yellowish oil.

Preparation of Compound (P-2):

Phosphono compound P-2 was synthesized according to method (A) described on page 305 in Tetrahedron, Vol. 30, by W. Lehnert. By using 6.71 grams of terephthalaldehyde and 23.11 grams of triethyl phosphonoacetate the desired product was obtained in yields of 89% (24.43 grams) as a pale brownish oil.

Preparation of Compound (P-3):

Phosphono compound P-3 was synthesized according to method (A) described on page 305 in Tetrahedron, Vol. 30, by W. Lehnert. By using 9.04 grams of 4-diethylamino-benzaldehyde and 12.71 grams of triethyl phosphonoacetate the desired product was obtained in yields of 17% (4.71 grams) as a yellow liquid.

Preparation of Compound (P-4):

Phosphono compound P-4 was synthesized according to method (A) described on page 305 in Tetrahedron, Vol. 30, by W. Lehnert. By using 9.11 grams of syringhaldehyde and 12.33 grams of triethyl phosphonoacetate the desired product was obtained in yields of 40% (7.81 grams) as a yellowish powder. Melting point: 109.6° C.

Preparation of Compound (P-6):

Phosphono compound P-6 was synthesized according to method (A) described on page 305 in Tetrahedron, Vol. 30, by W. Lehnert. By using 0.85 grams of 4-methoxy-benzaldehyde and 2.00 grams of tetraethyl methylenediphosphonate the desired product was obtained as a pale orange oil.

Preparation of Compound (P-7):

Phosphono compound P-7 was synthesized according to method (A) described on page 305 in Tetrahedron, Vol. 30, by W. Lehnert. By using 4.56 grams of biphenyl-4-carbaldehyde and 6.17 grams of triethyl phosphonoacetate the desired product was obtained as a brownish oil.

Preparation of Compound (P-5):

Phosphono compound P-5 was synthesized according to method (A) described on page 305 in Tetrahedron, Vol. 30, by W. Lehnert. By using 1.14 grams of biphenyl-4-carbaldehyde and 2.00 grams of tetraethyl methylenediphosphonate 0.3 grams of the desired product were obtained yielding orange-brown crystals.

Preparation of Compound (P-17):

Phosphono compound P-17 was synthesized according to method (A) described on page 305 in Tetrahedron, Vol. 30, by W. Lehnert. By using 5.00 grams of 4-acetamidobenzaldehyde and 6.96 grams of triethyl phosphonoacetate 4.67 grams of the desired product were obtained yielding a yellowish liquid.

Preparation of Compound (P-19):

Phosphono compound P-20 was synthesized according to method (A) described on page 305 in Tetrahedron, Vol. 30, by W. Lehnert. By using 4.2 grams of 4,4-biphenyldicarboxoaldehyde and 9.86 grams of triethyl phosphonoacetate 5.1 grams of the desired product were obtained yielding beige crystals.

Preparation of Compound (P-20):

Phosphono compound P-21 was synthesized according to method (B) described on page 305 in Tetrahedron, Vol. 30, by W. Lehnert. By using 9.01 grams of 9-fluorenone and 22.42 grams of triethyl phosphonoacetate 6.0 grams of the desired product were obtained yielding yellow crystals.

Preparation of Compound (P-21):

Phosphono compound P-22 was synthesized according to method (A) described on page 305 in Tetrahedron, Vol. 30, by W. Lehnert. By using 5.00 grams of vanillin and 7.44 grams of triethyl phosphonoacetate 6.37 grams of the desired product were obtained yielding orangebrown crystals.

Preparation of Compound (P-22):

Phosphono compound P-23 was synthesized according to method (A) described on page 305 in Tetrahedron, Vol. 30, by W. Lehnert. By using 8.50 grams of 3,4,5-trimethoxybenzaldehyde and 9.71 grams of triethyl phosphonoacetate 11.78 grams of the desired product were obtained yielding colorless crystals.

Photostability

Measurement of Photostability

The method used for assessment of photostability is based on the irradiation of a highly diluted solution of the UV-filter. The analysis after certain doses of irradiation was performed by UV-spectroscopy. The concentration of the UV-absorber in ethanol is adjusted to values between $1 \cdot 10^{-5}$ and $1 \cdot 10^{-6}$ mol/l, such that the absorbance of the solution in cuvette of 1 cm optical pathlength is equal or smaller than 0.2. The mutual protection of filter molecules can be excluded under such conditions. FIG. 1 shows the experimental set-up for the irradiation of the samples.

Prior to irradiation of a sample the UVB-intensity at the sample position is measured with a UV-radiometer (RM-12, Dr. Gröbel Electronic GmbH). This radiometer was calibrated by comparison with a measurement of the spectral output of the metal halide lamp (including light guide and cut-off filter) using a wavelength-resolved radiometer (Gamma C11). Therefore the relationship of the reading of the RM-12 radiometer and the corresponding spectral output of the lamp is known, and one is able to determine the wavelength-resolved intensities by measuring the UVB-intensity. By changing the distance between the end of the light guide and the cuvette, the UVB-intensity can be varied in the range of 100 $\mu W/cm^2$ and 4500 $\mu W/cm^2$.

For sample irradiation the highest possible intensity was used (4.5 $mW/cm^2$ UVB-intensity measured with the Macam 103 radiometer). The irradiation time was varied from 0 to 180 min. The dose the sample has received after 180 minutes corresponds to 60 MED. During irradiation the sample was stirred. After certain intervals of irradiation, the samples were analysed in a UV-spectrometer (Perkin Elmer, Lambda 16).

From the absorbance values at each dose of irradiation the concentration may be calculated using Lambert-Beer's law. In order to get the half-life of the substance, a first order kinetic model was fitted to the experimental data. Since the UV-spectrum of the lamp and the UV-spectrum of the COLIPA standard sun are known, one can calculate the respective half-life of the UV-absorber under conditions of COLIPA standard sun irradiation [Bernd Herzog, Stefan Müller, Myriam Sohn, Uli Osterwalder, "New Insight and Prediction of Photostablity of Sunscreens", SÖFW Journal 133, 26-36 (2007)].

The investigated half-time values and recovery after irradiation (10 MED) of some specific benzotropolones are listed in the table below:

| Comp. No. | Half time [h] | Recovery after 10MED [%] |
|---|---|---|
| (P-1) | 14 311 | 100 |
| (P-2) | 172 | 98.8 |
| (P-3) | 320 | 99.5 |
| (P-4) | 100 | 98.3 |
| (P-5) | 7 | 78 |
| (P-6) | 11285 | 99.98 |
| (P-7) | 466.6 | 99.6 |
| (P-17) | 947.6 | 99.8 |
| (P-19) | 220.6 | 99.2 |
| (P-20) | 449.2 | 99.6 |
| (P-22) | 262.8 | 99.3 |

The compounds Nos. P-1, P-2, P-3, P-4, P-6 and P-7 according to the present invention possess extraordinary high photostability and in all cases more than 98% of the arylidene phosphonates are recovered after irradiation of 10 MED. Even no photodegradation is observed for compound No. P-1 and No. P-7 after irradiation of 10 MED.

UV Shielding Properties

The UV shielding properties of the bisbiphenyl triazine derivatives were investigated by measuring their UV spectra in ethanol. In the following table the investigated absorption maxima ($\lambda_{max}$) together with the corresponding $A^{1\%}_{1cm}$ values are listed.

| | Absorption maximum | |
|---|---|---|
| Comp. No. | $\lambda_{max}$ | $A^{1\%}_{1\,cm}$ |
| (P-1) | 303 | 519 |
| (P-2) | 302 | 500 |
| (P-3) | 366 | 624 |

| Comp. No. | Absorption maximum | |
|---|---|---|
| | $\lambda_{max}$ | $A^{1\%}_{1\,cm}$ |
| (P-4) | 322 | 390 |
| (P-5) | 299 | 427 |
| (P-6) | 313 | 575 |
| (P-7) | 302 | 650 |
| (P-17) | 308 | 604 |
| (P-19) | 324 | 733 |
| (P-20) | 314 | 371 |
| (P-21) | 319 | 429 |
| (P-22) | 299 | 357 |

The phosphono compounds Nos. P-1, P-2, P-3, P-6 and P-7 according to the present invention possess good shielding properties in the UV region as indicated by $A^{1\%}_{1\,cm}$ values above 500. The phosphono compounds Nos. P-1, P-2, P-3, P-4, P-5, P-6 and P-7 exhibit broad absorption bands thus covering a broad area of the UV range and providing protection for a broad area of the UV range.

APPLICATION EXAMPLES

Application Example 1

O/W Sunscreen Formulation A

| | Trade Name | INCI-Name | % (w/w) |
|---|---|---|---|
| Part A | Amphisol K | Potassium Cetyl Phosphate | 1.80 |
| | Cutina GMS | Glyceryl Stearate | 2.50 |
| | Lanette 18 | Stearyl Alcohol | 2.50 |
| | Paraffin | Mineral Oil | 5.00 |
| | Compound (P-01) | | 2.00 |
| | Tegosoft TN | C12-15 Alkyl Benzoate | 8.00 |
| | Parsol 1789 | Butyl Methoxydibenzoylmethane | 2.00 |
| Part B | Water | Aqua | 65.10 |
| | Rhodicare S | Xanthan Gum | 0.30 |
| | Glycerin | Glycerin | 10.00 |
| Part C | Phenonip | Phenoxyethanol (and) Methylparaben (and) Ethylparaben (and) Butylparaben (and) Propylparaben (and) Isobutylparaben | 0.80 |

Manufacturing Instruction:

Prepare the part A and part B separately and heat to 75° C. Under increasing stirring incorporate part B to part A and homogenize with Ultra Turrax for 10 sec. at 10000 rpm. Let cool down to room temperature under stirring. At room temperature adjust pH between 5.80 and 6.20.

The photostability of Butyl Methoxydibenzoylmethane is determined by spreading the emulsion as a 20 µm thick film on a quartz plate. The film is irradiated using a solar simulator for 2 hours (5400 kJ/m2). After irradiation, the quartz plate is plunged into 5 ml of tetrahydrofurane. The amount of UV-A filter Butyl Methoxydibenzoylmethane is then determined using high performance liquid chromatography. The residual Butyl Methoxydibenzoylmethane is determined to be 42%.

O/W Sunscreen Formulation B (Comparative)

| | Trade Name | INCI-Name | % (w/w) |
|---|---|---|---|
| Part A | Amphisol K | Potassium Cetyl Phosphate | 1.80 |
| | Cutina GMS | Glyceryl Stearate | 2.50 |
| | Lanette 18 | Stearyl Alcohol | 2.50 |
| | Paraffin | Mineral Oil | 5.00 |
| | Tegosoft TN | C12-15 Alkyl Benzoate | 10.00 |
| | Parsol 1789 | Butyl Methoxydibenzoylmethane | 2.00 |
| Part B | Water | Aqua | 65.10 |
| | Rhodicare S | Xanthan Gum | 0.30 |
| | Glycerin | Glycerin | 10.00 |
| Part C | Phenonip | Phenoxyethanol (and) Methylparaben (and) Ethylparaben (and) Butylparaben (and) Propylparaben (and) Isobutylparaben | 0.80 |

The formulation is prepared as described for formulation A.

The photostability of Butyl Methoxydibenzoylmethane in the comparative formulation B is determined as described above for formulation A. The residual Butyl Methoxydibenzoylmethane is determined to be 4%. This means that Butyl Methoxydibenzoylmethane is significantly stabilized through the phosphono benzylidene compound (P-01) by a factor of at least 10.

Application Example 2

O/W Sunscreen Formulation A

| | Trade Name | INCI-Name | % (w/w) |
|---|---|---|---|
| Part A | Amphisol K | Potassium Cetyl Phosphate | 1.80 |
| | Cutina GMS | Glyceryl Stearate | 2.50 |
| | Lanette 18 | Stearyl Alcohol | 2.50 |
| | Paraffin | Mineral Oil | 5.00 |
| | Compound (P-01) | | 2.00 |
| | Tegosoft TN | C12-15 Alkyl Benzoate | 8.00 |
| | Uvinul MC80 | Ethylhexyl Methoxycinnemate | 2.00 |
| Part B | Water | Aqua | 65.10 |
| | Rhodicare S | Xanthan Gum | 0.30 |
| | Glycerin | Glycerin | 10.00 |
| Part C | Phenonip | Phenoxyethanol (and) Methylparaben (and) Ethylparaben (and) Butylparaben (and) Propylparaben (and) Isobutylparaben | 0.80 |

Manufacturing Instruction:

Prepare the part A and part B separately and heat to 75° C. Under increasing stirring incorporate part B to part A and homogenize with Ultra Turrax for 10 sec. at 10000 rpm. Let cool down to room temperature under stirring. At room temperature adjust pH between 5.80 and 6.20.

The photostability of the UV-B filter Ethylhexyl Methoxycinnemate is determined by spreading the emulsion as a 20 µm thick film on a quartz plate. The film is irradiated using a solar simulator for 4 hours (10800 kJ/m2). After irradiation, the quartz plate is plunged into 5 ml of tetrahydrofurane. The amount of UV-B filter Ethylhexyl Methoxycinnemate is then determined using high performance liquid chromatography. The residual Ethylhexyl Methoxycinnemate is determined to be 59%.

O/W Sunscreen Formulation B (Comparative)

|  | Trade Name | INCI-Name | % (w/w) |
|---|---|---|---|
| Part A | Amphisol K | Potassium Cetyl Phosphate | 1.80 |
|  | Cutina GMS | Glyceryl Stearate | 2.50 |
|  | Lanette 18 | Stearyl Alcohol | 2.50 |
|  | Paraffin | Mineral Oil | 5.00 |
|  | Tegosoft TN | C12-15 Alkyl Benzoate | 10.00 |
|  | Uvinul MC80 | Ethylhexyl Methoxycinnemate | 2.00 |
| Part B | Water | Aqua | 65.10 |
|  | Rhodicare S | Xanthan Gum | 0.30 |
|  | Glycerin | Glycerin | 10.00 |
| Part C | Phenonip | Phenoxyethanol (and) Methylparaben (and) Ethylparaben (and) Butylparaben (and) Propylparaben (and) Isobutylparaben | 0.80 |

The formulation is prepared as described for formulation A.

The photostability of Ethylhexyl Methoxycinnemate in the comparative formulation B is determined as described above for formulation A. The residual Ethylhexyl Methoxycinnemate is determined to be 38%. This means that Ethylhexyl Methoxycinnemate is significantly stabilized through the phosphono benzylidene compound (P-01) by a factor of 1.55.

The invention claimed is:

1. A method of protecting of human and animal hair and skin from UV radiation comprising applying to the skin or hair of a human or animal in need thereof the compounds of formula

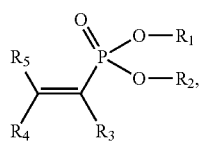

(1)

wherein
$R_1$ and $R_2$ independently of one another are hydrogen; unsubstituted or substituted $C_1$-$C_{12}$alkyl; unsubstituted or substituted $C_3$-$C_{12}$cycloalkyl; unsubstituted or substituted $C_6$-$C_{20}$aryl; or unsubstituted or substituted $C_2$-$C_{20}$alkenyl;
$R_3$ is $PO_3R_1R_2$; $COOR_6$; $COR_7$; $CONR_7R_8$; —$SO_2R_6$; CN; unsubstituted or substituted $C_6$-$C_{20}$aryl;
$R_4$ is unsubstituted $C_6$-$C_{20}$aryl; or $C_6$-$C_{20}$aryl which is substituted by at least one $C_1$-$C_{18}$alkyl, $C_1$-$C_{18}$alkoxy, $C_3$-$C_{12}$cycloalkyl, hydroxy, amino, mono- or di-$C_1$-$C_{18}$alkylamino, —$NR_{10}COR_{11}$ or the radical of formula

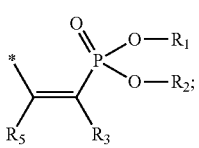

(1a)

or unsubstituted or substituted $C_4$-$C_{20}$heteroaryl;
$R_5$ is hydrogen; substituted or unsubstituted $C_1$-$C_{20}$alkyl; unsubstituted or substituted $C_3$-$C_{12}$cycloalkyl; unsubstituted or substituted $C_6$-$C_{20}$aryl; or unsubstituted or substituted $C_4$-$C_{20}$heteroaryl; or $R_4$ and $R_5$ form a cycloaliphatic ring;
$R_6$, $R_7$ and $R_8$ independently from each other are hydrogen; $C_1$-$C_{18}$alkyl or $C_3$-$C_{12}$cycloalkyl, which may be substituted by one or more E and/or interrupted by one or more D; or $C_6$-$C_{20}$aryl, which may be substituted by G; or
$R_7$ and $R_8$ together form a five or six membered ring;
D is —CO—; —COO—; —S—; —SO—; —$SO_2$—; —O—; —$NR_9$—; —$SiR_{12}R_{13}$—; —$POR_{14}$—; —$CR_{15}$=$CR_{16}$—; or —C≡C—;
E is —$OR_{17}$; —$SR_{17}$; —$NR_{10}R_{11}$; —$NR_{10}COR_{11}$; —$COR_{11}$; —$COOR_{11}$; —$CONR_{10}R_{11}$; —CN; halogen; $SO_3R_{18}$; $SO_2R_{18}$; $PO_3(R_{18})_2$; or $PO_2(R_{18})_2$;
G is E; $C_1$-$C_{18}$alkyl, which is optionally interrupted by D; $C_1$-$C_{18}$perfluoroalkyl; $C_1$-$C_{18}$alkoxy, which is optionally substituted by E and/or interrupted by D; wherein
$R_9$, $R_{10}$ and $R_{11}$, independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or
$R_{10}$ and $R_{11}$ together form a five or six membered ring;
$R_{12}$ and $R_{13}$ independently of each other are hydrogen; $C_1$-$C_{18}$alkyl; or $C_6$-$C_{18}$aryl which is optionally substituted by $C_1$-$C_{18}$alkyl;
$R_{14}$ is $C_1$-$C_{18}$alkyl; or $C_6$-$C_{18}$aryl, which is optionally substituted by $C_1$-$C_{18}$alkyl;
$R_{15}$ and $R_{16}$ independently of each other are hydrogen; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;
$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—; and
$R_{18}$ is hydrogen; $C_6$-$C_{18}$aryl, which is optionally substituted by $C_1$-$C_{18}$alkyl or $C_1$-$C_{18}$alkoxy; or $C_1$-$C_{18}$alkyl, which is optionally interrupted by —O—.

2. The method according to claim 1, wherein
$R_1$ and $R_2$ independently of one another are hydrogen; or $C_1$-$C_{12}$alkyl.

3. The method according to claim 1, wherein
$R_3$ is $PO_3R_1R_2$; $COOR_6$; $COR_7$; or $SO_2R_6$; wherein
$R_1$ and $R_2$, independently from each other are hydrogen; or unsubstituted or substituted $C_1$-$C_{12}$alkyl; and
$R_6$ and $R_7$ independently from each other are unsubstituted or substituted $C_1$-$C_{18}$alkyl or $C_6$-$C_{20}$aryl.

4. The method according to claim 1, wherein
$R_4$ is unsubstituted $C_6$-$C_{20}$aryl; or $C_6$-$C_{20}$aryl which is substituted by at least one $C_1$-$C_{18}$alkyl, $C_1$-$C_{18}$alkoxy, hydroxy, mono- or di-$C_1$-$C_{18}$alkylamino or the radical of formula

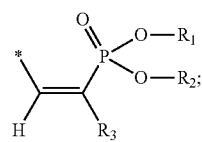

(1a)

wherein
$R_1$ and $R_2$ independently from each other are unsubstituted $C_1$-$C_{12}$alkyl;
$R_3$ is $COOR_6$; and
$R_6$ is $C_1$-$C_5$alkyl.

5. The method according to claim 1, wherein
$R_5$ is hydrogen; or $C_1$-$C_{20}$alkyl.

6. The method according to claim 1, wherein compounds of formula

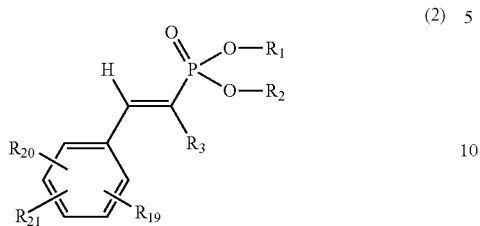 (2)

are used, wherein
- $R_1$ and $R_2$ independently from each other are $C_1$-$C_5$alkyl;
- $R_3$ is —$COOR_6$; $SO_2R_6$; $PO_3R_1R_2$; $COR_6$; unsubstituted $C_6$-$C_{10}$aryl; or $C_6$-$C_{10}$aryl which is substituted by $C_1$-$C_5$alkyl or $C_1$-$C_5$alkoxy;
- $R_6$ is $C_1$-$C_5$alkyl; or $C_6$-$C_{10}$aryl;
- $R_{19}$, $R_{20}$ and $R_{21}$, independently from each other are hydrogen; $C_1$-$C_5$alkyl; $C_1$-$C_5$alkoxy; amino; $C_1$-$C_5$-dialkylamino; phenyl; or a radical of formula

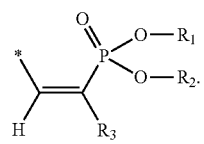

* * * * *